(12) United States Patent
Mackay et al.

(10) Patent No.: US 11,053,319 B2
(45) Date of Patent: Jul. 6, 2021

(54) CXCR2 ANTIBODIES AND USES THEREOF

(71) Applicant: Monash University, Clayton (AU)

(72) Inventors: Charles Reay Mackay, Clayton (AU); Remy Michel Robert, Clayton (AU)

(73) Assignee: Monash University, Clayton (AU)

(*) Notice: Subject to any disclaimer, the term of this patent is extended or adjusted under 35 U.S.C. 154(b) by 171 days.

(21) Appl. No.: 15/907,208

(22) Filed: Feb. 27, 2018

(65) Prior Publication Data

US 2019/0016809 A1    Jan. 17, 2019

(30) Foreign Application Priority Data

Feb. 27, 2017 (AU) ............................... 2017900656

(51) Int. Cl.
| | | |
|---|---|---|
| *C07K 16/28* | (2006.01) | |
| *A61P 29/00* | (2006.01) | |
| *A61P 35/00* | (2006.01) | |

(52) U.S. Cl.
CPC .......... *C07K 16/2866* (2013.01); *A61P 29/00* (2018.01); *A61P 35/00* (2018.01); *C07K 2317/24* (2013.01); *C07K 2317/34* (2013.01); *C07K 2317/56* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,440,021 A | 8/1995 | Chuntharapai et al. |
| 10,253,111 B2 * | 4/2019 | Elias ....................... A61P 31/04 |

FOREIGN PATENT DOCUMENTS

| WO | WO-2012/062713 A1 | 5/2012 |
| WO | WO-2013/168108 A2 | 11/2013 |
| WO | WO-2014/170317 A1 | 10/2014 |
| WO | WO-2015/169811 A2 | 11/2015 |
| WO | WO-2018/154391 A1 | 8/2018 |

OTHER PUBLICATIONS

Boshuizen, R. S. et al. (2014). "A combination of in vitro techniques for efficient discovery of functional monoclonal antibodies against human CXC chemokine receptor-2 (CXCR2)", mAbs, vol. 6, No. 6, pp. 1415-1424.
International Preliminary Report on Patentability issued in International Application No. PCT/IB2018/000253, dated Aug. 27, 2019 (dated Aug. 27, 2019). 8 pages.
International Search Report issued in International Application No. PCT/162018/000253, dated Jun. 8, 2018 (dated Jun. 8, 2018). 9 pages.
Extended European Search Report issued in European Patent Application No. 18758109.5 , dated Dec. 1, 2020 (dated Dec. 1, 2020), 25 pages.
Wu, Lijun et al. (1996). "Discrete Steps in Binding and Signaling of Interleukin-8 with Its Receptor," *Journal of Biological Chemistry*, vol. 271, No. 49, Dec. 6, 1996 (Dec. 6, 1996), pp. 31202-31209, XP055753014, US ISSN: 0021-9258, DOI: 10.1074/jbc.271.49. 31202.

* cited by examiner

*Primary Examiner* — Michael D Pak

(74) *Attorney, Agent, or Firm* — Mintz, Levin, Cohn, Ferris, Glovsky and Popeo, P.C.

(57) ABSTRACT

The invention relates to CXCR2, to antibodies and related fragments thereof for binding to CXCR2, to production of said antibodies and fragments and to use of said antibodies and fragments for detection and therapy of various conditions.

4 Claims, 10 Drawing Sheets

Specification includes a Sequence Listing.

CXCR2 ANTIBODIES AND USES THEREOF

CROSS REFERENCE TO RELATED APPLICATIONS

This application claims priority to Australian Provisional Application No. AU 2017900656, filed Feb. 27, 2017, which is hereby incorporated by reference in its entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 048517-532001US_ST25.TXT, created on Feb. 27, 2018, having 29,599 bytes, machine format IBM-PC, MS Windows operating system, is hereby incorporated by reference.

BACKGROUND OF THE INVENTION

Chemokines or chemoattractant cytokines comprise a family of inducible secreted molecules of small molecular weight (~8-10 KDa) which typically function as activators and chemoattractants to leukocytes and can modulate angiogenesis, wound healing, and tumorigenesis Most of the knowledge of chemokine functions is derived from research on the immune system due to their implication in regulation of immune coordination and inflammation. Roles involving many other biological systems are slowly being elucidated.

Chemokines are typically classified into four subfamilies according to the number of conserved cysteine residues in their amino terminus. Most chemokines fit into two main subfamilies with four cysteine residues. These subfamilies are typically classified according to the presence or absence of an amino acid between the two amino terminus cysteine residues, and are thus named CC and CXC chemokines. CXC chemokines, which are typically restricted to higher vertebrates, are usually further classified according to the presence or absence of a glutamate-lysine-arginine (ELR) motif on their amino terminus adjacent to the first cysteine residue. CXCL1, previously known as Gro-α, is a member of the ELR family of CXC chemokines whose preferred receptor is CXCR2.

The CXCR's N-terminus domain is thought to be important for determining ligand binding specificity. CXCR2 binds CXCL1, a soluble secreted chemoattractive cytokine of the ELR positive family of CXC chemokines, and their interaction activates intracellular signals that modulate processes such as proliferation, differentiation, and migration. Changes in migration are thought to take effect by the modulation of actin-dependent cellular processes and adhesion molecule expression. Upon binding its ligands in the vasculature, CXCR2 modulates adhesion molecule expression on the surface of some leukocytes to allow their rolling adhesion, arrest, and diapedesis for tissue infiltration. This is commonly observed in monocytes and neutrophils expressing the chemokine receptor CXCR2. Once in the tissue, these cells are typically further guided by chemokines to inflammatory sites by chemotaxis.

Although each chemokine receptor usually binds a single class of chemokines, they can bind several members of the same class with high affinity. In addition, one chemokine can bind several different chemokine receptors. CXCR2, for example, can bind CXCL1, CXCL2, CXCL3, CXCL5, CXCL6, CXCL7, and CXCL8.

CXCR2 is a class A GPCR belonging to the chemokine receptor family with a size of ~41 kDa. CXCR2 is the only high-affinity receptor for all pro-angiogenic chemokines (CXCL1-3, CXCL5-8). CXCL6 and CXCL8 (IL-8) elicit their chemotactic effects by interacting also with CXCR1. Physiologically, CXCR2 is involved in the mobilization and recruitment of leukocytes (especially neutrophils) from the bone marrow to sites of inflammation and the migration of endothelial cells in angiogenesis.

The expression of CXCR2 on a variety of cells and tissues including CD8+ T cells, NK, monocytes, mast cells, epithelial, endothelial, smooth muscle and a host of cell types in the central nervous system suggests that this receptor may have a broad functional role under both constitutive conditions and in the pathophysiology of a number of acute and chronic diseases. Once activated, CXCR2 is phosphorylated and is rapidly internalized through arrestin/dynamin-dependent mechanisms, resulting in receptor desensitization. CXCR2 and its ligands have been reported to be overexpressed by various tumours and overexpression is often associated with poor prognosis.

There exists a need for new and/or improved inhibitors of CXCR2 which can be used to treat diseases associated with CXCR2 activation.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

BRIEF SUMMARY OF THE INVENTION

The present invention provides an antigen binding site (e.g., a paratope of an antibody, antibody variant or fragment thereof) that binds to or specifically binds to CXCR2 and inhibits CXCR2 activity.

Preferably, the antigen binding site comprises an antigen binding domain of an antibody, the antigen binding domain binds to or specifically binds to CXCR2 and inhibits CXCR2 activity.

The CXCR2 activity that may be inhibited by any antigen binding site of the invention includes: ligand binding to CXCR2; ligand induced conformational change of CXCR2; CXCR2 activation; G protein activation; CXCR2 mediated cell signalling; a CXCR2 mediated cell migratory, inflammatory, tumour growth, angiogenic or metastatic response in vitro or in vivo; CXCR2 mediated tumour cell growth; and/or CXCR2 mediated leukocyte (e.g. neutrophil, eosinophil, mast cell or T cell) migration.

Preferably, the antigen binding site of the invention binds to or specifically binds to human CXCR2. Preferably, the antigen binding site binds to or specifically binds to a human CXCR2 molecule comprising, consisting essentially of or consisting of an amino acid sequence as shown in SEQ ID NO: 52.

Preferably, the antigen binding site inhibits or reduces the CXCR2 activity induced by any ligand including CXCL1, CXCL2, CXCL3, CXCL5 and/or CXCL6. For example, the antigen binding site may inhibit the migration of cell, preferably immune cells, stimulated by a CXCR2 ligand. Reduction or inhibition of CXCR2 activity may be determined by any method as described herein, particularly Example 3.

An antigen binding site of the invention may bind to CXCR2 and not detectably bind to or bind significantly to CCR6, CXCR1, CXCR2 and/or CXCR7. The binding of an antigen binding site to CXCR1, CXCR2 and/or CXCR7 may be determined by any method described herein, particularly flow cytometry as described in Example 2.

An antigen binding site of the invention may bind to CXCR2 and exhibit an $EC_{50}$ of less than 2 nM. Preferably, the $EC_{50}$ is determined using a flow cytometry or ELISA assay as described herein, particularly Example 2.

An antigen binding site of the invention may exhibit an $IC_{50}$ in a competition binding assay with CXCL3 of less than about 20, 15, 12, 10, 8, 6, 5, 4, 3, 2, or 1 nM. Preferably, the $IC_{50}$ is a value as described herein. Preferably, the competition binding assay is performed by any method as described herein, particularly Example 3.

An antigen binding site of the invention may exhibit an $EC_{50}$ in migration assay with CXCL1, CXCL2 and/or CXCL5 of less than about 20, 15, 12, 10, 8, 6, 5, 4, 3, 2, or 1 nM. Preferably, the $EC_{50}$ is a value as described herein. Preferably, the migration assay is performed by any method as described herein, particularly Example 3.

An antigen binding site of the invention may inhibit the migration of an immune cell expressing CXCR2 to CXCL6 at concentrations of 10 µg/ml, 1 µg/ml or less. Preferably, the migration assay is performed by any method as described herein, particularly Example 3.

An antigen binding site of the invention may bind to CXCR2 within residues 10 to 21 (numbering as per human CXCR2 or SEQ ID NO:52). Preferably, residues 10 to 21 are SFEDFWKGEDLS (SEQ ID NO:60). Preferably, the antigen binding site binds within residues 10 to 21 and no other residues within the first 46 residues of CXCR2 (e.g., SEQ ID NO:52).

An antigen binding site of the invention may bind to a peptide consisting of the amino acid sequence of SEQ ID NO: 52 and a further peptide consisting of the amino acid sequence of SEQ ID NO: 53, however it does not detectably bind to a peptide consisting of the amino acid sequence of SEQ ID NO: 54.

The present invention also provides an antigen binding site which binds to an N-terminal region of CXCR2 and inhibits CXCL2, CXCL3 and/or CXCL6 binding to, or CXCL2, CXCL3 and/or CXCL6 mediated activity of, CXCR2. Preferably, the N-terminal region comprises, consists essentially of or consists of residues 10 to 21 (numbering as per human CXCR2). Preferably, residues 10 to 21 are SFEDFWKGEDLS (SEQ ID NO:60). Preferably, the antigen binding site binds within residues 10 to 21 and no other residues within the first 46 residues of CXCR2. Preferably, the CXCL2, CXCL3 and/or CXCL6 mediated activity is CXCL2, CXCL3 and/or CXCL6 mediated chemotaxis of an immune cell (e.g. neutrophil). Preferably, the antigen binding site also inhibits CXCL1 binding to, or CXCL1 mediated activity of, CXCR2.

The invention provides an antigen binding site for binding to CXCR2, the antigen binding site comprising:
FR1-CDR1-FR2-CDR2-FR3-CDR3-FR4-linker-FR1a-CDR1a-FR2a-CDR2a-FR3a-CDR3a-FR4a
wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein the sequence of any of the framework regions or complementarity determining regions are as described herein.

The invention provides an antigen binding site for binding to CXCR2, the antigen binding site including:
FR1-CDR1-FR2-CDR2-FR3-CDR3-FR4-linker-FR1a-CDR1a-FR2a-CDR2a-FR3a-CDR3a-FR4a
wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein the sequence of any of the complementarity determining regions have an amino acid sequence as described in Table 1 below. Preferably, the framework regions have an amino acid sequence also as described in Table 1 below, including amino acid variation at particular residues which can be determined by aligning the various framework regions derived from each antibody. The invention also includes where CDR1, CDR2 and CDR3 are sequences from the VH, CDR1a, CDR2a and CDR3a are sequences from VL, or where CDR1, CDR2 and CDR3 are sequences from the VL, CDR1a, CDR2a and CDR3a are sequences from VH.

The invention provides an antigen binding site comprising, consisting essentially of or consisting of an amino acids sequence of (in order of N to C terminus or C to N terminus):
SEQ ID NO: 7 and 8;
SEQ ID NO: 17 and 18;
SEQ ID NO: 27 and 28; and/or
SEQ ID NO: 31 and 32.

The present invention also provides an antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:4, a CDR2 comprising a sequence at least about 80%, at least 85%, at least 90%, at least 92%, at least 95%, at least 97%, at least 99% identical to a sequence set in SEQ ID NO:5 and a CDR3 comprising a sequence at least about 80%, at least 85%, at least 90%, at least 92%, at least 95%, at least 97%, at least 99% identical to a sequence set forth in SEQ ID NO: 6;
(ii) a VH comprising a sequence at least about 95% or 96% or 97% or 98% or 99% identical to a sequence set forth in SEQ ID NO: 8 or 32;
(iii) a VL comprising a CDR1 comprising a sequence at least about 80%, at least 85%, at least 90%, at least 92%, at least 95%, at least 97%, at least 99% identical to a sequence set forth in SEQ ID NO: 1, a CDR2 comprising a sequence at least about 80%, at least 85%, at least 90%, at least 92%, at least 95%, at least 97%, at least 99% identical to a sequence set forth in SEQ ID NO: 2 and a CDR3 comprising a sequence at least about 80%, at least 85%, at least 90%, at least 92%, at least 95%, at least 97%, at least 99% identical to a sequence set forth in SEQ ID NO: 3;
(iv) a VL comprising a sequence at least about 95% identical to a sequence set forth in SEQ ID NO: 7 or 31;
(v) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6;
(vi) a VH comprising a sequence set forth in SEQ ID NO: 8 or 32;

(vii) a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3;
(viii) a VL comprising a sequence set forth in SEQ ID NO: 7 or 31;
(ix) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6; and a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3;
(x) a VH comprising a sequence set forth in SEQ ID NO: 8 and a VL comprising a sequence set forth in SEQ ID NO: 7; or
(xi) a VH comprising a sequence set forth in SEQ ID NO: 32 and a VL comprising a sequence set forth in SEQ ID NO: 31.

The present invention also provides an antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:14, a CDR2 comprising a sequence at least about 80%, at least 85%, at least 90%, at least 92%, at least 95%, at least 97%, at least 99% identical to a sequence set in SEQ ID NO:15 and a CDR3 comprising a sequence at least about 80%, at least 85%, at least 90%, at least 92%, at least 95%, at least 97%, at least 99% identical to a sequence set forth in SEQ ID NO: 16;
(ii) a VH comprising a sequence at least about 95% or 96% or 97% or 98% or 99% identical to a sequence set forth in SEQ ID NO: 18;
(iii) a VL comprising a CDR1 comprising a sequence at least about 80%, at least 85%, at least 90%, at least 92%, at least 95%, at least 97%, at least 99% identical to a sequence set forth in SEQ ID NO: 11, a CDR2 comprising a sequence at least about 80%, at least 85%, at least 90%, at least 92%, at least 95%, at least 97%, at least 99% identical to a sequence set forth in SEQ ID NO: 12 and a CDR3 comprising a sequence at least about 80%, at least 85%, at least 90%, at least 92%, at least 95%, at least 97%, at least 99% identical to a sequence set forth in SEQ ID NO: 13;
(iv) a VL comprising a sequence at least about 95% identical to a sequence set forth in SEQ ID NO: 17;
(v) a VH comprising a CDR1 comprising a sequence set forth in SEQ ID NO: 14, a CDR2 comprising a sequence set forth between in SEQ ID NO: 15 and a CDR3 comprising a sequence set forth in SEQ ID NO: 16;
(vi) a VH comprising a sequence set forth in SEQ ID NO: 18;
(vii) a VL comprising a CDR1 comprising a sequence set SEQ ID NO: 11, a CDR2 comprising a sequence set forth in SEQ ID NO: 12 and a CDR3 comprising a sequence set forth in SEQ ID NO: 13;
(viii) a VL comprising a sequence set forth in SEQ ID NO: 17;
(ix) a VH comprising a CDR1 comprising a sequence set forth in SEQ ID NO: 14, a CDR2 comprising a sequence set forth between in SEQ ID NO: 15 and a CDR3 comprising a sequence set forth in SEQ ID NO: 16; and a VL comprising a CDR1 comprising a sequence set SEQ ID NO: 11, a CDR2 comprising a sequence set forth in SEQ ID NO: 12 and a CDR3 comprising a sequence set forth in SEQ ID NO: 13; or
(x) a VH comprising a sequence set forth in SEQ ID NO: 18 and a VL comprising a sequence set forth in SEQ ID NO: 17.

The present invention also provides an antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) comprising a sequence at least about 80%, at least 85%, at least 90%, at least 92%, at least 95%, at least 97%, at least 99% identical to a sequence set forth in SEQ ID NO:24, a CDR2 comprising a sequence at least about 80%, at least 85%, at least 90%, at least 92%, at least 95%, at least 97%, at least 99% identical to a sequence set in SEQ ID NO: 25 and a CDR3 comprising a sequence at least about 80%, at least 85%, at least 90%, at least 92%, at least 95%, at least 97%, at least 99% identical to a sequence set forth in SEQ ID NO: 26;
(ii) a VH comprising a sequence at least about 95% or 96% or 97% or 98% or 99% identical to a sequence set forth in SEQ ID NO: 28;
(iii) a VL comprising a CDR1 comprising a sequence at least about 80%, at least 85%, at least 90%, at least 92%, at least 95%, at least 97%, at least 99% identical to a sequence set forth in SEQ ID NO: 21, a CDR2 comprising a sequence at least about 80%, at least 85%, at least 90%, at least 92%, at least 95%, at least 97%, at least 99% identical to a sequence set forth in SEQ ID NO: 22 and a CDR3 comprising a sequence at least about 80%, at least 85%, at least 90%, at least 92%, at least 95%, at least 97%, at least 99% identical to a sequence set forth in SEQ ID NO: 23;
(iv) a VL comprising a sequence at least about 95% identical to a sequence set forth in SEQ ID NO: 27;
(v) a VH comprising a CDR1 comprising a sequence set forth in SEQ ID NO: 24, a CDR2 comprising a sequence set forth between in SEQ ID NO: 25 and a CDR3 comprising a sequence set forth in SEQ ID NO: 26;
(vi) a VH comprising a sequence set forth in SEQ ID NO: 28;
(vii) a VL comprising a CDR1 comprising a sequence set SEQ ID NO: 21, a CDR2 comprising a sequence set forth in SEQ ID NO: 22 and a CDR3 comprising a sequence set forth in SEQ ID NO: 23;
(viii) a VL comprising a sequence set forth in SEQ ID NO: 27;
(ix) a VH comprising a CDR1 comprising a sequence set forth in SEQ ID NO: 24, a CDR2 comprising a sequence set forth between in SEQ ID NO: 25 and a CDR3 comprising a sequence set forth in SEQ ID NO: 26; and a VL comprising a CDR1 comprising a sequence set SEQ ID NO: 21, a CDR2 comprising a sequence set forth in SEQ ID NO: 22 and a CDR3 comprising a sequence set forth in SEQ ID NO: 23; or
(x) a VH comprising a sequence set forth in SEQ ID NO: 28 and a VL comprising a sequence set forth in SEQ ID NO: 27.

In any aspect of the invention, the antigen binding domain further comprises at least one of:
(i) a VH comprising a framework region (FR) 1 comprising a sequence at least about 80%, at least 85%, at least 90%, at least 92%, at least 95%, at least 97%, at least 99% identical to a sequence set forth in SEQ ID NO:40 or 48, a FR2 comprising a sequence at least about 80%, at least 85%, at least 90%, at least 92%, at least 95%, at least 97%, at least 99% identical to a sequence set in SEQ ID NO:41 or 49, a FR3 comprising a sequence at least about 80%, at least 85%, at least 90%, at least 92%, at least 95%, at least 97%, at least 99% identical to a sequence set forth in SEQ ID NO: 42 or 50, and a FR4 comprising a sequence at least about 80%, at least 85%, at least 90%, at least 92%, at least 95%, at least 97%, at least 99% identical to a sequence set forth in SEQ ID NO: 43 or 51;
(ii) a VL comprising a FR1 comprising a sequence at least about 80%, at least 85%, at least 90%, at least 92%, at least 95%, at least 97%, at least 99% identical to a sequence set forth in SEQ ID NO: 33, 34, 35 or 44, a FR2 comprising a sequence at least about 80%, at least 85%, at least 90%, at least 92%, at least 95%, at least 97%, at least 99% identical to a sequence set forth in SEQ ID NO: 36 or 45, a FR3 comprising a sequence at least about 80%, at least 85%, at least 90%, at least 92%, at least 95%, at least 97%, at least 99% identical to a sequence set forth in SEQ ID NO: 37, 38 or 46, and a FR4 comprising a sequence at least about 80%, at least 85%, at least 90%, at least 92%, at least 95%, at least 97%, at least 99% identical to a sequence set forth in SEQ ID NO: 39 or 47;
(iii) a VH comprising a FR1 comprising a sequence set forth in SEQ ID NO: 40 or 48, a FR2 comprising a sequence set forth between in SEQ ID NO: 41 or 49, a FR3 comprising a sequence set forth in SEQ ID NO: 42 or 50, and a FR4 comprising a sequence set forth in SEQ ID NO: 43 or 51;
(iv) a VL comprising a FR1 comprising a sequence set forth in SEQ ID NO: 33, 34, 35 or 44, a FR2 comprising a sequence set forth between in SEQ ID NO: 36 or 45, a FR3 comprising a sequence set forth in SEQ ID NO: 37, 38 or 46, and a FR4 comprising a sequence set forth in SEQ ID NO: 39 or 47; or
(v) a VH comprising a FR1 comprising a sequence set forth in SEQ ID NO: 40 or 48, a FR2 comprising a sequence set forth between in SEQ ID NO: 41 or 49, a FR3 comprising a sequence set forth in SEQ ID NO: 42 or 50, and a FR4 comprising a sequence set forth in SEQ ID NO: 43 or 51; and a VL comprising a FR1 comprising a sequence set forth in SEQ ID NO: 33, 34, 35 or 44, a FR2 comprising a sequence set forth between in SEQ ID NO: 36 or 45, a FR3 comprising a sequence set forth in SEQ ID NO: 37, 38 or 46, and a FR4 comprising a sequence set forth in SEQ ID NO: 39 or 47.

As described herein, the antigen binding site may be in the form of:
(i) a single chain Fv fragment (scFv);
(ii) a dimeric scFv (di-scFv);
(iii) one of (i) or (ii) linked to a constant region of an antibody, Fc or a heavy chain constant domain (CH) 2 and/or CH3; or
(iv) one of (i) or (ii) linked to a protein that binds to an immune effector cell.

Further, as described herein, the antigen binding site may be in the form of:
(i) a diabody;
(ii) a triabody;
(iii) a tetrabody;
(iv) a Fab;
(v) a F(ab')2;
(vi) a Fv;
(vii) one of (i) to (vi) linked to a constant region of an antibody, Fc or a heavy chain constant domain (CH) 2 and/or CH3; or
(viii) one of (i) to (vi) linked to a protein that binds to an immune effector cell.

The foregoing antigen binding sites can also be referred to as antigen binding domains of antibodies.

Preferably, an antigen binding site as described herein is an antibody or antigen binding fragment thereof. Typically, the antigen binding site is an antibody, for example, a monoclonal antibody.

As used herein the antigen binding site may be a variable domain.

The present invention also provides a C-X-C motif chemokine receptor 2 (CXCR2) antibody comprising a light chain variable region and a heavy chain variable region, wherein said light chain variable region comprises: a CDR L1 as set forth in SEQ ID NO:1, a CDR L2 as set forth in SEQ ID NO:2 and a CDR L3 as set forth in SEQ ID NO:3; and wherein said heavy chain variable region comprises: a CDR H1 as set forth in SEQ ID NO:4, a CDR H2 as set forth in SEQ ID NO:5, and a CDR H3 as set forth in SEQ ID NO:6.

The present invention also provides a C-X-C motif chemokine receptor 2 (CXCR2) antibody comprising a light chain variable region and a heavy chain variable region, wherein said light chain variable region comprises: a CDR L1 as set forth in SEQ ID NO:11, a CDR L2 as set forth in SEQ ID NO:12 and a CDR L3 as set forth in SEQ ID NO:13; and wherein said heavy chain variable region comprises: a CDR H1 as set forth in SEQ ID NO:14, a CDR H2 as set forth in SEQ ID NO:15, and a CDR H3 as set forth in SEQ ID NO:16.

The present invention also provides a C-X-C motif chemokine receptor 2 (CXCR2) antibody comprising a light chain variable region and a heavy chain variable region, wherein said light chain variable region comprises: a CDR L1 as set forth in SEQ ID NO:21, a CDR L2 as set forth in SEQ ID NO:22 and a CDR L3 as set forth in SEQ ID NO:23; and wherein said heavy chain variable region comprises: a CDR H1 as set forth in SEQ ID NO:24, a CDR H2 as set forth in SEQ ID NO:25, and a CDR H3 as set forth in SEQ ID NO:26.

In any aspect of the invention, the antigen binding site or C-X-C motif chemokine receptor 2 (CXCR2) antibody comprises a light chain variable region that comprises: a Val or Asp at a position corresponding to Kabat position 1; an Ile, Val or Ala at a position corresponding to Kabat position 2; a Thr, Ala or Ser at a position corresponding to Kabat position 7; a Ser or Thr at a position corresponding to Kabat position 14; a Leu or Pro at a position corresponding to Kabat position 15; an Asp or Glu at a position corresponding to Kabat position 17; a Gln or Pro at a position corresponding to Kabat position 18; a Lys or Gln at a position corresponding to Kabat position 45; a Ser or Ala at a position corresponding to Kabat position 67; a Leu or Val at a position corresponding to Kabat position 83; and/or a Gly or Gln at a position corresponding to Kabat position 100.

In any aspect of the invention, the antigen binding site or C-X-C motif chemokine receptor 2 (CXCR2) antibody comprises a heavy chain variable region that comprises: a Gln or Val at a position corresponding to Kabat position 5; a Pro or Ala at a position corresponding to Kabat position 9; a Leu or Val at a position corresponding to Kabat position 11; a Val or Lys at a position corresponding to Kabat position 12; an Ile or Val at a position corresponding to Kabat position 20; a Lys or Arg at a position corresponding to Kabat position 38; an Arg or Ala at a position corresponding to Kabat position 40; a Lys or Gln at a position corresponding to Kabat position 43; a Lys or Arg at a position corresponding to Kabat position 44; a Ser or Ala at a position corresponding to Kabat position 75; a Gln or Glu at a position corresponding to Kabat position 81; a Thr or Arg at a position corresponding to Kabat position 83; and/or a Ser or Thr at a position corresponding to Kabat position 87.

In any aspect of the invention, a CXCR2 antibody comprises a light chain variable region that comprises the sequence of SEQ ID NO:7, SEQ ID NO:17, SEQ ID NO:27 or NO:31.

In any aspect of the invention, a CXCR2 antibody comprises a heavy chain variable region that comprises the sequence of SEQ ID NO:8, SEQ ID NO:18, SEQ ID NO:28 or NO:32.

In any aspect of the invention, a CXCR2 antibody comprises a light chain variable region that comprises a FR L1 as set forth in SEQ ID NO:33, FR L2 as set forth in SEQ ID NO:36, a FR L3 as set forth in SEQ ID NO:37 and a FR L4 as set forth in SEQ ID NO:39.

In any aspect of the invention, a CXCR2 antibody comprises a light chain variable region that comprises a FR L1 as set forth in SEQ ID NO:34, FR L2 as set forth in SEQ ID NO:36, a FR L3 as set forth in SEQ ID NO:37 and a FR L4 as set forth in SEQ ID NO:39.

In any aspect of the invention, a CXCR2 antibody comprises a light chain variable region that comprises a FR L1 as set forth in SEQ ID NO:35, FR L2 as set forth in SEQ ID NO:36, a FR L3 as set forth in SEQ ID NO:38 and a FR L4 as set forth in SEQ ID NO:39.

In any aspect of the invention, a CXCR2 antibody comprises a light chain variable region that comprises a FR L1 as set forth in SEQ ID NO:44, FR L2 as set forth in SEQ ID NO:45, a FR L3 as set forth in SEQ ID NO:46 and a FR L4 as set forth in SEQ ID NO:47.

In any aspect of the invention, a CXCR2 antibody comprises a heavy chain variable region that comprises a FR H1 as set forth in SEQ ID NO:40, FR H2 as set forth in SEQ ID NO:41, a FR H3 as set forth in SEQ ID NO:42 and a FR H4 as set forth in SEQ ID NO:43.

In any aspect of the invention, a CXCR2 antibody comprises a heavy chain variable region that comprises a FR H1 as set forth in SEQ ID NO:48, FR H2 as set forth in SEQ ID NO:49, a FR H3 as set forth in SEQ ID NO:50 and a FR H4 as set forth in SEQ ID NO:51.

In any aspect or embodiment, the antibody is a naked antibody. Specifically, the antibody is in a non-conjugated form and is not adapted to form a conjugate.

In embodiments, the CXCR2 antibody is a humanized antibody. In embodiments, the CXCR2 antibody is a chimeric antibody. In embodiments, the CXCR2 antibody is a Fab' fragment. In embodiments, the CXCR2 antibody is a single chain antibody (scFv).

In embodiments, the light chain variable region provided herein includes the sequence of SEQ ID NO:7, SEQ ID NO:17, SEQ ID NO:27 or NO:31. I In embodiments, the light chain variable region provided herein is the sequence of SEQ ID NO:7, SEQ ID NO:17, SEQ ID NO:27 or NO:31.

In embodiments, the heavy chain variable region provided herein includes the sequence of SEQ ID NO:8, SEQ ID NO:18, SEQ ID NO:28 or NO:32. In embodiments, the heavy chain variable region provided herein is the sequence of SEQ ID NO:8, SEQ ID NO:18, SEQ ID NO:28 or NO:32.

In an aspect, a C-X-C motif chemokine receptor 2 (CXCR2) antibody is provided. The antibody includes a light chain variable region and a heavy chain variable region, wherein the light chain variable region includes: a CDR L1 as set forth in SEQ ID NO:1, a CDR L2 as set forth in SEQ ID NO:2 and a CDR L3 as set forth in SEQ ID NO:3; and wherein the heavy chain variable region includes: a CDR H1 as set forth in SEQ ID NO:58, a CDR H2 as set forth in SEQ ID NO:5, and a CDR H3 as set forth in SEQ ID NO:6.

In embodiments, the light chain variable region includes: a Val or Asp at a position corresponding to Kabat position 1; an Ile, Val or Ala at a position corresponding to Kabat position 2; a Thr, Ala or Ser at a position corresponding to Kabat position 7; a Ser or Thr at a position corresponding to Kabat position 14; a Leu or Pro at a position corresponding to Kabat position 15; an Asp or Glu at a position corresponding to Kabat position 17; a Gln or Pro at a position corresponding to Kabat position 18; a Lys or Gln at a position corresponding to Kabat position 45; a Glu or Gln at a position corresponding to Kabat position 47; a Ser or Ala at a position corresponding to Kabat position 67; a Leu or Val at a position corresponding to Kabat position 83; and/or a Gly or Gln at a position corresponding to Kabat position 100.

In embodiments, the light chain variable region includes a Val or Asp at a position corresponding to Kabat position 1. In embodiments, the light chain variable region includes a Val at a position corresponding to Kabat position 1. In embodiments, the light chain variable region includes a Asp at a position corresponding to Kabat position 1.

In embodiments, the light chain variable region includes an Ile, Val or Ala at a position corresponding to Kabat position 2. In embodiments, the light chain variable region includes an Ile at a position corresponding to Kabat position 2. In embodiments, the light chain variable region includes a Val at a position corresponding to Kabat position 2. In embodiments, the light chain variable region includes an Ala at a position corresponding to Kabat position 2.

In embodiments, the light chain variable region includes a Thr, Ala or Ser at a position corresponding to Kabat position 7. In embodiments, the light chain variable region includes a Thr at a position corresponding to Kabat position 7. In embodiments, the light chain variable region includes an Ala at a position corresponding to Kabat position 7. In embodiments, the light chain variable region includes a Ser at a position corresponding to Kabat position 7.

In embodiments, the light chain variable region includes a Ser or Thr at a position corresponding to Kabat position 14. In embodiments, the light chain variable region includes a Ser at a position corresponding to Kabat position 14. In embodiments, the light chain variable region includes a Thr at a position corresponding to Kabat position 14.

In embodiments, the light chain variable region includes a Leu or Pro at a position corresponding to Kabat position 15. In embodiments, the light chain variable region includes a Leu at a position corresponding to Kabat position 15. In embodiments, the light chain variable region includes a Pro at a position corresponding to Kabat position 15.

In embodiments, the light chain variable region includes an Asp or Glu at a position corresponding to Kabat position 17. In embodiments, the light chain variable region includes an Glu at a position corresponding to Kabat position 17. In embodiments, the light chain variable region includes an Asp at a position corresponding to Kabat position 17.

In embodiments, the light chain variable region includes a Gln or Pro at a position corresponding to Kabat position 18. In embodiments, the light chain variable region includes a Gln at a position corresponding to Kabat position 18. In embodiments, the light chain variable region includes a Pro at a position corresponding to Kabat position 18.

In embodiments, the light chain variable region includes a Lys or Gln at a position corresponding to Kabat position 45. In embodiments, the light chain variable region includes a Lys at a position corresponding to Kabat position 45. In embodiments, the light chain variable region includes a Gln at a position corresponding to Kabat position 45.

In embodiments, the light chain variable region includes a Glu or Gln at a position corresponding to Kabat position 47. In embodiments, the light chain variable region includes a Glu at a position corresponding to Kabat position 47. In embodiments, the light chain variable region includes a Gln at a position corresponding to Kabat position 47.

In embodiments, the light chain variable region includes a Ser or Ala at a position corresponding to Kabat position 67. In embodiments, the light chain variable region includes a Ser at a position corresponding to Kabat position 67. In embodiments, the light chain variable region includes an Ala at a position corresponding to Kabat position 67.

In embodiments, the light chain variable region includes a Leu or Val at a position corresponding to Kabat position 83. In embodiments, the light chain variable region includes a Leu at a position corresponding to Kabat position 83. In embodiments, the light chain variable region includes a Val at a position corresponding to Kabat position 83.

In embodiments, the light chain variable region includes a Gly or Gln at a position corresponding to Kabat position 100. In embodiments, the light chain variable region includes a Gly at a position corresponding to Kabat position 100. In embodiments, the light chain variable region includes a Gln at a position corresponding to Kabat position 100.

In embodiments, the heavy chain variable region includes: a Gln or Val at a position corresponding to Kabat position 5; a Pro or Ala at a position corresponding to Kabat position 9; a Leu or Val at a position corresponding to Kabat position 11; a Val or Lys at a position corresponding to Kabat position 12; an Ile or Val at a position corresponding to Kabat position 20; a Lys or Arg at a position corresponding to Kabat position 38; an Arg or Ala at a position corresponding to Kabat position 40; a Lys or Gln at a position corresponding to Kabat position 43; a Lys or Arg at a position corresponding to Kabat position 44; a Ser or Ala at a position corresponding to Kabat position 75; a Gln or Glu at a position corresponding to Kabat position 81; a Thr or Arg at a position corresponding to Kabat position 83; and/or a Ser or Thr at a position corresponding to Kabat position 87.

In embodiments, the heavy chain variable region includes a Gln or Val at a position corresponding to Kabat position 5. In embodiments, the heavy chain variable region includes a Pro or Ala at a position corresponding to Kabat position 9. In embodiments, the heavy chain variable region includes a Leu or Val at a position corresponding to Kabat position 11. In embodiments, the heavy chain variable region includes a Val or Lys at a position corresponding to Kabat position 12. In embodiments, the heavy chain variable region includes an Ile or Val at a position corresponding to Kabat position 20. In embodiments, the heavy chain variable region includes a Lys or Arg at a position corresponding to Kabat position 38. In embodiments, the heavy chain variable region includes an Arg or Ala at a position corresponding to Kabat position 40. In embodiments, the heavy chain variable region includes a Lys or Gln at a position corresponding to Kabat position 43. In embodiments, the heavy chain variable region includes a Lys or Arg at a position corresponding to Kabat position 44. In embodiments, the heavy chain variable region includes a Ser or Ala at a position corresponding to Kabat position 75. In embodiments, the heavy chain variable region includes a Gln or Glu at a position corresponding to Kabat position 81. In embodiments, the heavy chain variable region includes a Thr or Arg at a position corresponding to Kabat position 83.

In embodiments, the heavy chain variable region includes and/or a Ser or Thr at a position corresponding to Kabat position 87.

In embodiments, the light chain variable region includes the sequence of SEQ ID NO:7, SEQ ID NO:17, SEQ ID NO:27, SEQ ID NO:31 and SEQ ID NO:57. In embodiments, the light chain variable region includes the sequence of SEQ ID NO:7. In embodiments, the light chain variable region includes the sequence of SEQ ID NO:17. In embodiments, the light chain variable region includes the sequence of SEQ ID NO:27. In embodiments, the light chain variable region includes the sequence of SEQ ID NO:31. In embodiments, the light chain variable region includes the sequence of SEQ ID NO:57.

In embodiments, the heavy chain variable region includes the sequence of SEQ ID NO:8, SEQ ID NO:18, SEQ ID NO:28, SEQ ID NO:32 or SEQ ID NO:56. In embodiments, the heavy chain variable region includes the sequence of SEQ ID NO:8. In embodiments, the heavy chain variable region includes the sequence of SEQ ID NO:18. In embodiments, the heavy chain variable region includes the sequence of SEQ ID NO:28. In embodiments, the heavy chain variable region includes the sequence of SEQ ID NO:32. In embodiments, the heavy chain variable region includes the sequence of SEQ ID NO:56.

In embodiments, the light chain variable region comprises a FR L1 as set forth in SEQ ID NO:44, FR L2 as set forth in SEQ ID NO:59, a FR L3 as set forth in SEQ ID NO:46 and a FR L4 as set forth in SEQ ID NO:47.

In embodiments, the CXCR2 antibody is an IgG. In embodiments, the CXCR2 antibody is an IgG4.

In an aspect is provided an isolated antibody, which binds the same epitope as a CXCR2 antibody, wherein the heavy chain variable region of the CXCR2 antibody is encoded by SEQ ID NO:10 and the light chain variable region of the CXCR2 antibody is encoded by SEQ ID NO:9.

In an aspect is provided an isolated antibody, which binds the same epitope as a CXCR2 antibody, wherein the heavy chain variable region of the CXCR2 antibody is encoded by SEQ ID NO:20 and the light chain variable region of the CXCR2 antibody is encoded by SEQ ID NO:19.

In an aspect is provided an isolated antibody, which binds the same epitope as a CXCR2 antibody, wherein the heavy chain variable region of the CXCR2 antibody is encoded by SEQ ID NO:30 and the light chain variable region of the CXCR2 antibody is encoded by SEQ ID NO:29.

In an aspect is provided an isolated nucleic acid encoding a CXCR2 antibody as provided herein including embodiments thereof.

In an aspect is provided a pharmaceutical composition including a therapeutically effective amount of a CXCR2 antibody as provided herein including embodiments thereof and a pharmaceutically acceptable excipient.

In an aspect is provided a cell including a CXCR2 antibody as provided herein including embodiments thereof.

In an aspect is provided a method of treating an inflammatory disease or cancer in a subject in need thereof, the method including administering to a subject a therapeutically effective amount of a CXCR2 antibody as provided herein including embodiments thereof, thereby treating the inflammatory disease or cancer in the subject. In embodiments, the disease is cancer. In embodiments, the disease is an inflammatory disease.

In one example, the complementarity determining region sequences (CDRs) of an antigen binding site of the invention are defined according to the Kabat numbering system.

In another example, the CDRs are defined according to the IMGT numbering system.

Reference herein to a protein or antibody that "binds to" CXCR2 provides literal support for a protein or antibody that "binds specifically to" or "specifically binds to" CXCR2.

The present invention also provides antigen binding domains or antigen binding fragments of the foregoing antibodies.

The invention also provides a fusion protein comprising an antigen binding site, immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multispecific antibody as described herein.

The invention also provides a conjugate in the form of an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody or fusion protein as described herein conjugated to a label or a cytotoxic agent.

The invention also provides an antibody for binding to an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein, or conjugate as described herein.

The invention also provides a nucleic acid encoding an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

In one example, such a nucleic acid is included in an expression construct in which the nucleic acid is operably linked to a promoter. Such an expression construct can be in a vector, e.g., a plasmid.

In examples of the invention directed to single polypeptide chain antigen binding sites, the expression construct may comprise a promoter linked to a nucleic acid encoding that polypeptide chain.

In examples directed to multiple polypeptide chains that form an antigen binding site, an expression construct comprises a nucleic acid encoding a polypeptide comprising, e.g., a VH operably linked to a promoter and a nucleic acid encoding a polypeptide comprising, e.g., a VL operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide,
wherein the first polypeptide comprises a VH and the second polypeptide comprises a VL, or vice versa.

The present invention also contemplates separate expression constructs one of which encodes a first polypeptide comprising a VH and another of which encodes a second polypeptide comprising a VL. For example, the present invention also provides a composition comprising:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter.

The invention provides a cell comprising a vector or nucleic acid described herein. Preferably, the cell is isolated, substantially purified or recombinant. In one example, the cell comprises the expression construct of the invention or:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter,
wherein the first and second polypeptides associate to form an antigen binding site of the present invention.

Examples of cells of the present invention include bacterial cells, yeast cells, insect cells or mammalian cells.

The invention also provides a pharmaceutical composition comprising an antigen binding site, or comprising a CDR and/or FR sequence as described herein, or an immunoglobulin variable domain, antibody, dab (single domain antibody), di-scFv, scFv, Fab, Fab', F(ab')2, Fv fragment, diabody, triabody, tetrabody, linear antibody, single-chain antibody molecule, or multispecific antibody, fusion protein, or conjugate as described herein and a pharmaceutically acceptable carrier, diluent or excipient.

The invention also provides a diagnostic composition comprising an antigen binding site, or comprising a CDR and/or FR sequence as described herein, or antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein, a diluent and optionally a label.

The invention also provides a kit or article of manufacture comprising an antigen binding site, or comprising a CDR and/or FR sequence as described herein or an immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

An antigen binding site, a protein or antibody as described herein may comprise a human constant region, e.g., an IgG constant region, such as an IgG1, IgG2, IgG3 or IgG4 constant region or mixtures thereof. In the case of an antibody or protein comprising a VH and a VL, the VH can be linked to a heavy chain constant region and the VL can be linked to a light chain constant region.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington D.C. United States Department of Health and Human Services, 1987 and/or 1991)).

In one example a protein or antibody as described herein or a composition of a protein or antibody as described herein, comprises a heavy chain constant region, comprising a stabilized heavy chain constant region, comprising a mixture of sequences fully or partially with or without the C-terminal lysine residue.

In one example, an antibody of the invention comprises a VH disclosed herein linked or fused to an IgG4 constant region or stabilized IgG4 constant region (e.g., as discussed above) and the VL is linked to or fused to a kappa light chain constant region.

The functional characteristics of an antigen binding site of the invention will be taken to apply mutatis mutandis to an antibody of the invention.

An antigen binding site as described herein may be purified, substantially purified, isolated and/or recombinant.

An antigen binding site of the invention may be part of a supernatant taken from media in which a hybridoma expressing an antigen binding site of the invention has been grown.

The present invention also provides a method for treating or preventing an inflammatory disease or cancer in a subject, the method comprising administering an antigen binding site of the invention. In this regard, an antigen binding site can be used to prevent a relapse of a condition, and this is considered preventing the condition.

Exemplary cancers include hematologic cancers, cancers of epithelial origin, liver cancer, pancreatic cancer, gastric cancer, osteosarcoma, endometrial cancer and ovarian cancer.

The invention also provides a cell comprising a vector or nucleic acid molecule described herein.

The invention also provides an animal or tissue derived therefrom comprising a cell described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 1 shows the results of the flow cytometry experiments. All antibodies, 3H9 (panel A), CM2 (panel B) and 6G7 (panel C), bound to cells expressing human CXCR2, however none of the antibodies showed any significant binding to human CCR6, CXCR1, CXCR3 or CXCR7 as the flow cytometry staining was identical to that observed with cells not expressing any chemokine receptor. Results in order from back to front for each of the histograms shown in panel A, B and C, respectively, are hCCR6, hCXCR1, hCXCR2, hCXCR3, hCXCR7 and L1.2 cells not transfected with any chemokine receptor.

DETAILED DESCRIPTION OF THE INVENTION

Definitions

Figure 1:
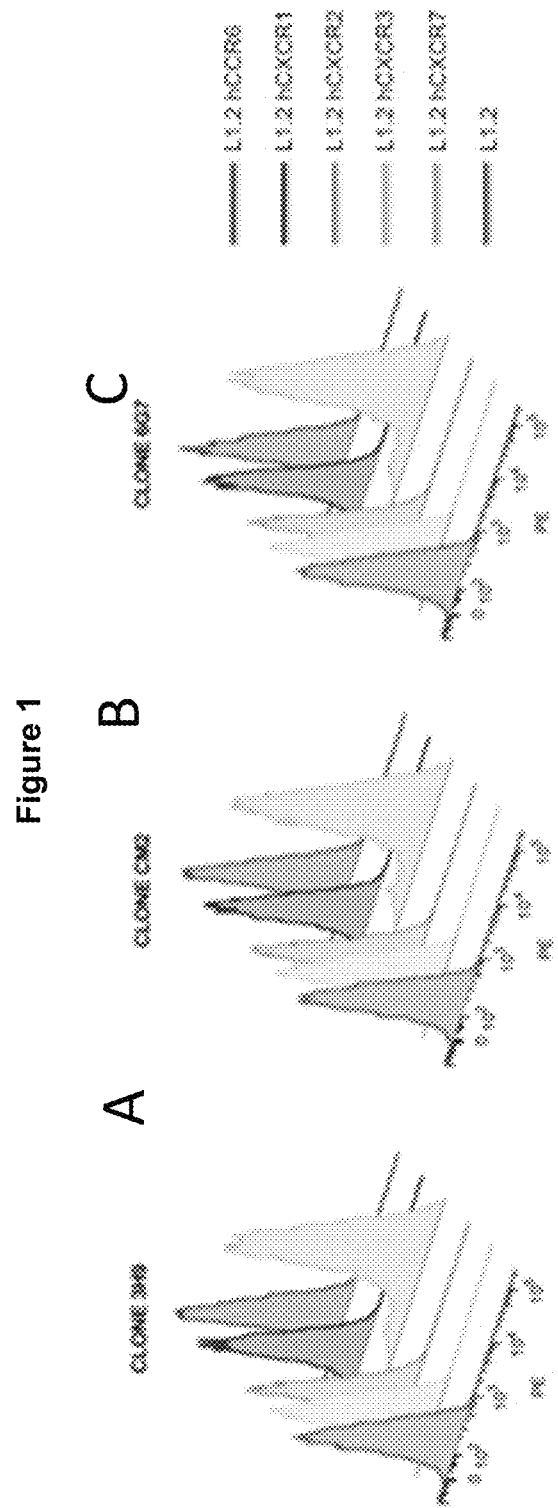
FIG. 1. Receptor binding specificity of the antibodies.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

The present inventors have developed antigen binding sites, for example antibodies, that bind to and inhibit or reduce the activity of CXCR2. The antigen binding sites as described herein have the capacity to inhibit or reduce one or more aspects of the inflammatory, tumour growth and metastatic activity mediated by CXCR2.

I. General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects, and vice versa, unless the context clearly dictates otherwise. For example, reference to "a" includes a single as well as two or more; reference to "an" includes a single as well as two or more; reference to "the" includes a single as well as two or more and so forth.

Those skilled in the art will appreciate that the present invention is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

The present invention is not to be limited in scope by the specific examples described herein, which are intended for the purpose of exemplification only. Functionally-equivalent products, compositions and methods are clearly within the scope of the present invention.

Any example or embodiment of the present invention herein shall be taken to apply mutatis mutandis to any other example or embodiment of the invention unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

"The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue.

An amino acid residue in an antibody "corresponds" to a given residue when it occupies the same essential structural position within the antibody as the given residue. For example, a selected residue in a comparison antibody corresponds to position 1 (according to the Kabat numbering system as described herein) in an antibody provided herein when the selected residue occupies the same essential spatial or structural relationship to Kabat position 1 as assessed using applicable methods in the art. For example, a comparison antibody may be aligned for maximum sequence homology with the antibody provided herein and the position in the aligned comparison antibody that aligns with Kabat position 1 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 1 in the structural model may be said to correspond.

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

The term "and/or", e.g., "X and/or Y" shall be understood to mean either "X and Y" or "X or Y" and shall be taken to provide explicit support for both meanings or for either meaning.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

II. Selected Definitions

CXCR2 is also known as C-X-C motif chemokine receptor 2 (CD182; IL8R2; IL8RA; IL8RB; CMKAR2; CDw128b). CXCR2 is a G protein-coupled receptor (GPCR) that is expressed on many different cells and tissues, including neutrophils, mast cells, CD8+ T cells, epithelial, endothelial, smooth muscle, and a variety of cell types in the central nervous system. Several high-affinity ligands have been identified, CXCL1 (growth-related oncogene α [GRO-α]), CXCL8 (interleukin-8), and CXCL5 (ENA-78) as well as lower affinity ligands CXCL2 (GRO-β), CXCL3 (GRO-γ), CXCL6 (GCP-2), and CXCL7 (NAP-2).

The term "CXCR2" as provided herein includes any of the C-X-C motif chemokine receptor 2 (CXCR2) protein naturally occurring forms, homologs or variants that maintain the activity of CXCR2 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CXCR2 protein is the protein as identified by the UniProt sequence reference P25025, homolog or functional fragment thereof.

For the purposes of nomenclature only and not a limitation, an exemplary amino acid sequence of human CXCR2 is SEQ ID NO: 52.

As used herein, reference to CXCR2 is to a molecule that has at least one biochemical or biophysical activity of CXCR2; CXCR2 biochemical or biophysical activities include acute inflammatory response to antigenic stimulus cell surface receptor signaling pathway, cellular defense response, chemotaxis, dendritic cell chemotaxis, inflammatory response, metanephric tubule morphogenesis, midbrain development, negative regulation of neutrophil apoptotic process, neutrophil activation, neutrophil chemotaxis, phospholipase C-activating G-protein coupled receptor signaling pathway, positive regulation of angiogenesis, positive regulation of cardiac muscle cell apoptotic process, positive regulation of cell proliferation, positive regulation of cytosolic calcium ion concentration positive regulation of neutrophil chemotaxis, positive regulation of vascular permeability, receptor internalization, and signal transduction.

The phrase "inhibits CXCR2 activity" is understood to mean that the antigen binding site of the present invention inhibits or reduces any one or more activities of CXCR2, including but not limited to ligand binding to CXCR2; ligand induced conformational change of CXCR2; CXCR2 activation; G protein activation; CXCR2 mediated cell signalling; a CXCR2 mediated cell migratory, inflammatory, tumour growth, angiogenic or metastatic response in vitro or in vivo; CXCR2 mediated tumour cell growth; and/or CXCR2 mediated leukocyte (e.g. neutrophil, eosinophil, mast cell or T cell) migration. "Inhibits CXCL2, CXCL3 and/or CXCL6 mediated CXCR2 activity" is understood to mean that the antigen binding site of the present invention inhibits or reduces one or more activities described above that are mediated or induced by CXCL2, CXCL3 and/or CXCL6. Further, the activity is measured using a suitable in vitro, cellular or in vivo assay and the activity is blocked or reduced by at least 1%, 5%, 10%, 25%, 50%, 60%, 70%, 80% or 90% or more, compared to CXCR2 activity in the same assay under the same conditions but without the antigen binding site. Preferably, the CXCR2 activity is mediated or induced by any one or more ligands, for example, high-affinity ligands CXCL1 (growth-related oncogene α [GRO-α]), CXCL8 (interleukin-8), and CXCL5 (ENA-78) or lower affinity ligands CXCL2 (GRO-β), CXCL3 (GRO-γ), CXCL6 (GCP-2), and CXCL7 (NAP-2). Most preferably, the CXCR2 activity is mediated or induced by CXCL2, 3 and/or 6.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include, but are not limited to, yeast cells and cells derived from plants and animals, for example mammalian, insect (e.g., *spodoptera*) and human cells.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "antigen binding site" is used interchangeably with "antigen binding domain" and shall be taken to mean a region of an antibody that is capable of specifically binding to an antigen, i.e., a VH or a VL or an Fv comprising both a VH and a VL. The antigen binding domain need not be in the context of an entire antibody, e.g., it can be in isolation (e.g., a domain antibody) or in another form, e.g., as described herein, such as a scFv.

The term "antigen" as provided herein refers to molecules capable of binding to the antibody binding domain provided herein. An "antigen binding domain" as provided herein is a region of an antibody that binds to an antigen (epitope). As described above, the antigen binding domain is generally composed of one constant and one variable domain of each of the heavy and the light chain (VL, VH, CL and CHL respectively). The paratope or antigen-binding site is formed on the N-terminus of the antigen binding domain. The two variable domains of an antigen binding domain typically bind the epitope on an antigen.

For the purposes for the present disclosure, the term "antibody" includes a protein capable of specifically binding to one or a few closely related antigens (e.g., CXCR2) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region (VH or VL wherein each are ~110 amino acids in length) and one or more constant domains at the C-terminus. The constant domain of the light chain (CL which is ~110 amino acids in length) is aligned with and disulfide bonded to the first constant domain of the heavy chain (CH1 which is 330 to 440 amino acids in length). The light chain variable region is aligned with the variable region of the heavy chain. The antibody heavy chain can comprise 2 or more additional CH domains (such as, CH2, CH3 and the like) and can comprise a hinge region between the CH1 and CH2 constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody", "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, monospecific Fab2, bispecific Fab2, trispecific Fab3, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain (VH or VL) typically has three CDRs identified as CDR1, CDR2 and CDR3. The CDRs of VH are also referred to herein as CDR H1, CDR H2 and CDR H3, respectively, wherein CDR H1 corresponds to CDR 1 of VH, CDR H2 corresponds to CDR 2 of VH and CDR H3 corresponds to CDR 3 of VH. Likewise, the CDRs of VL are referred to herein as CDR L1, CDR L2 and CDR L3, respectively, wherein CDR L1 corresponds to CDR 1 of VL, CDR L2 corresponds to CDR 2 of VL and CDR L3 corresponds to CDR 3 of VL.

The CDRs of the variable region of the light chain are further referred to herein as LCDR1, LCDR2 and LCDR3, respectively, wherein LCDR1 corresponds to CDR 1 of VL, LCDR 2 corresponds to CDR 2 of VL and LCDR 3 corresponds to CDR 3 of VL (e.g., Table 1). Likewise, the CDRs of the variable region of the heavy chain are further referred to herein as HCDR1, HCDR2 and HCDR3, respectively, wherein HCDR1 corresponds to CDR 1 of VH, HCDR 2 corresponds to CDR 2 of VH and HCDR 3 corresponds to CDR 3 of VH.

In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). The present invention is not limited to FRs and CDRs as defined by the Kabat numbering system, but includes all numbering systems, including the canonical numbering system or of Chothia and Lesk J. Mol. Biol. 196: 901-917, 1987; Chothia et al., Nature 342: 877-883, 1989; and/or Al-Lazikani et al., J. Mol. Biol. 273: 927-948, 1997; the numbering system of Honnegher and Plükthun J. Mol. Biol. 309: 657-670, 2001; or the IMGT system discussed in Giudicelli et al., Nucleic Acids Res. 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In this regard, Padlan et al., FASEB J., 9: 133-139, 1995 established that the five C-terminal amino acids of heavy chain CDR2 are not generally involved in antigen binding.

"Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of the variable region of the heavy chain are further referred to herein as HFR1, HFR2, HFR3 and HFR4, respectively, wherein HFR1 corresponds to FR 1 of VH, HFR 2 corresponds to FR 2 of VH, HFR 3 corresponds to FR 3 of VH and HFR 4 corresponds to FR 4 of VH.

Likewise, the FRs of VL are referred to herein as FR L1, FR L2, FR L3 and FR L4, respectively, wherein FR L1 corresponds to FR 1 of VL, FR L2 corresponds to FR 2 of VL, FR L3 corresponds to FR 3 of VL and FR L4 corresponds to FR 4 of VL. Likewise, the FRs of the variable region of the light chain are further referred to herein as LFR1, LFR2, LFR3 and LFR4, respectively, wherein LFR1 corresponds to FR 1 of VL, LFR 2 corresponds to FR 2 of VL, LFR 3 corresponds to FR 3 of VL and LFR 4 corresponds to FR 4 of VL.

As used herein, the term "Fv" shall be taken to mean any protein, whether comprised of multiple polypeptides or a single polypeptide, in which a VL and a VH associate and form a complex having an antigen binding domain, i.e., capable of specifically binding to an antigen. The VH and the VL which form the antigen binding domain can be in a single polypeptide chain or in different polypeptide chains. Furthermore, an Fv of the invention (as well as any protein of the invention) may have multiple antigen binding domains which may or may not bind the same antigen. This term shall be understood to encompass fragments directly derived from an antibody as well as proteins corresponding to such a fragment produced using recombinant means. In some examples, the VH is not linked to a heavy chain constant domain (CH) 1 and/or the VL is not linked to a light chain constant domain (CL). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., CH2 or CH3 domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a VH and a single constant domain. Two Fab' fragments are obtained per antibody treated in this manner. A Fab' fragment can also be produced by recombinant means. A "F(ab)2 fragment" of an antibody consists of a dimer of two Fab' fragments held together by two disulfide bonds, and is obtained by treating a whole antibody molecule with the enzyme pepsin, without subsequent reduction. A "Fab2" fragment is a recombinant fragment comprising two Fab fragments linked using, for example a leucine zipper or a CH3 domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of an antigen binding site or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that an antigen binding site of the invention reacts or associates more frequently, more rapidly, with greater duration and/or with greater affinity with a particular antigen or cell expressing same than it does with alternative antigens or cells. For example, an antigen binding site binds to CXCR2 (e.g., hCXCR2) with materially greater affinity (e.g., 1.5 fold or 2 fold or 5 fold or 10 fold or 20 fold or 40 fold or 60 fold or 80 fold to 100 fold or 150 fold or 200 fold) than it does to other CXCRs. In an example of the present invention, an antigen binding site that "specifically binds" to CXCR2 (preferably human) with an affinity at least 1.5 fold or 2 fold or greater (e.g., 5 fold or 10 fold or 20 fold r 50 fold or 100 fold or 200 fold) than it does to another chemokine receptor, such as CXCR1, CXCR3, CXCR7 or CCR6. Generally, but not necessarily, reference to binding means specific binding, and each term shall be understood to provide explicit support for the other term.

As used herein, the term "does not detectably bind" shall be understood to mean that an antigen binding site, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the antigen binding site is immobilized and contacted with an antigen.

As used herein, the term "does not significantly bind" shall be understood to mean that the level of binding of an antigen binding site of the invention to a polypeptide is not statistically significantly higher than background, e.g., the level of binding signal detected in the absence of the antigen binding site and/or in the presence of a negative control protein (e.g., an isotype control antibody) and/or the level of binding detected in the presence of a negative control polypeptide. The level of binding is detected using biosensor analysis (e.g. Biacore) in which the antigen binding site is immobilized and contacted with an antigen.

A "ligand" refers to an agent, e.g., a polypeptide or other molecule, capable of binding to a receptor or antibody, antibody variant, antibody region or fragment thereof.

As used herein, the term "epitope" (syn. "antigenic determinant") shall be understood to mean a region of CXCR2 to which an antigen binding site comprising an antigen binding domain of an antibody binds. Unless otherwise defined, this term is not necessarily limited to the specific residues or structure to which the antigen binding site makes contact. For example, this term includes the region spanning amino acids contacted by the antigen binding site and 5-10 (or more) or 2-5 or 1-3 amino acids outside of this region. In some examples, the epitope comprises a series of discontinuous amino acids that are positioned close to one another when antigen binding site is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics. In embodiments the epitope includes SEQ ID NO:53. In embodiments the epitope includes SEQ ID NO:55.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. antibodies and antigens) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

As used herein, the term "condition" refers to a disruption of or interference with normal function, and is not to be limited to any specific condition, and will include diseases or disorders.

As defined herein, the term "inhibition", "inhibit", "inhibiting" and the like in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

As used herein, the terms "preventing", "prevent" or "prevention" include administering an antigen binding site of the invention to thereby stop or hinder the development of at least one symptom of a condition. This term also encompasses treatment of a subject in remission to prevent or hinder relapse.

As used herein, the terms "treating", "treat" or "treatment" include administering an antigen binding site described herein to thereby reduce or eliminate at least one symptom of a specified disease or condition. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

As used herein, the term "subject" shall be taken to mean any animal including humans, for example a mammal. Exemplary subjects include but are not limited to humans and non-human primates. For example, the subject is a human.

Antibodies

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

In one example, an antigen binding site or CXCR2-binding protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods CXCR2 (e.g., hCXCR2) or a region thereof (e.g., an extracellular region) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, subcutaneously, intravenously, intradermally, intraperitoneally, or by other known route.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention.

Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

Monoclonal antibodies are one exemplary form of antibody contemplated by the present invention. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies, for example, which do not express murine antibodies, can also be used to generate an antibody of the present invention (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods.* 197: 85-95, 1996).

A humanized antibody is a genetically engineered antibody in which at least one CDR (or functional fragment thereof) from a mouse antibody ("donor antibody", which can also be rat, hamster or other non-human species) are grafted onto a human antibody ("acceptor antibody"). The human antibody is a non-natural (e.g. not naturally occurring or not naturally produced by a human) antibody that does not elicit an immune response in a human, does not elicit a significant immune response in a human, or elicits an immune response that is less than the immune response elicited in a mouse. In embodiments, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and a variable region framework (FR). The FR may form part of a constant region and/or a variable region within a human antibody. In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g. the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g. as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Typically a humanized antibody as provided herein may include (i) a light chain comprising at least one CDR (often three CDRs) from a mouse antibody (also referred to herein as a mouse CDR) and a human variable region framework; and (ii) a heavy chain comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody.

A "therapeutic agent" as referred to herein, is a composition useful in treating or preventing a disease such as cancer (e.g., leukemia). In embodiments, the therpaeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

The antibody of the present invention may be a synthetic antibody. For example, the antibody is a chimeric antibody, a humanized antibody, a human antibody synhumanized antibody, primatized antibody or a de-immunized antibody.
Antibody Binding Domain Containing Proteins
Single-Domain Antibodies In some examples, a protein of the invention is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, a protein of the invention is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ (SEQ ID NO:61) being one of the more favored linkers for a scFv.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present invention encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Proteins Comprising Antigen Binding Domains Thereof

The present invention also contemplates other antibodies and proteins comprising antigen-binding domains thereof, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) $Fab_3$ (e.g., as described in EP19930302894).

Mutations to Proteins

The present invention also provides an antigen binding site or a nucleic acid encoding same having at least 80% identity to a sequence disclosed herein. In one example, an antigen binding site or nucleic acid of the invention comprises sequence at least about 85% or 90% or 95% or 97% or 98% or 99% identical to a sequence disclosed herein.

Alternatively, or additionally, the antigen binding site comprises a CDR (e.g., three CDRs) at least about 80% or 85% or 90% or 95% or 97% or 98% or 99% identical to CDR(s) of a $V_H$ or $V_L$ as described herein according to any example.

In another example, a nucleic acid of the invention comprises a sequence at least about 80% or 85% or 90% or 95% or 97% or 98% or 99% identical to a sequence encoding an antigen binding site having a function as described herein according to any example. The present invention also encompasses nucleic acids encoding an antigen binding site of the invention, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present invention also contemplates a nucleic acid that hybridizes under stringent hybridization conditions to a nucleic acid encoding an antigen binding site described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present invention also contemplates mutant forms of an antigen binding site of the invention comprising one or more conservative amino acid substitutions compared to a sequence set forth herein. In some examples, the antigen binding site comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical is that the same primers can be used to amplify the sequence.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.*, 157: 105-132, 1982 and hydrophylic indices are described in, e.g., U.S. Pat. No. 4,554,101.

The present invention also contemplates non-conservative amino acid changes. For example, of particular interest are substitutions of charged amino acids with another charged amino acid and with neutral or positively charged amino acids. In some examples, the antigen binding site comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an antigen binding site of the invention. In another example, the mutation(s) occur within a CDR of an antigen binding site of the invention.

Exemplary methods for producing mutant forms of an antigen binding site include:
  mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology*, 7: 18, 2007; and WO1999/058661);
  introducing a nucleic acid encoding the polypeptide into a mutator cell, e.g., XL-1Red, XL-mutS and XL-mutS-Kanr bacterial cells (Stratagene);
  DNA shuffling, e.g., as disclosed in Stemmer, *Nature* 370: 389-91, 1994; and
  site directed mutagenesis, e.g., as described in Dieffenbach (ed) and Dveksler (ed) (In: PCR Primer: A Laboratory Manual, Cold Spring Harbor Laboratories, N Y, 1995).

Exemplary methods for determining biological activity of the mutant antigen binding sites of the invention will be apparent to the skilled artisan and/or described herein, e.g., antigen binding. For example, methods for determining antigen binding, competitive inhibition of binding, affinity, association, dissociation and therapeutic efficacy are described herein.

Constant Regions

The present invention encompasses antigen binding sites and/or antibodies described herein comprising a constant region of an antibody. This includes antigen binding fragments of an antibody fused to an Fc.

Sequences of constant regions useful for producing the proteins of the present invention may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., *Proc. Natl. Acad. USA*, 63, 78-85, 1969). In human IgG4, this residue is generally a serine. Following substitution of the serine for proline, the IgG4 hinge region comprises a sequence CPPC (SEQ ID NO:62). In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (SEQ ID NO:62) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immunol.* 29:2613-2624, 1999; Shields et al., *J Biol Chem.* 276(9):6591-604, 2001). Additional examples of non-immunostimulatory Fc regions are described, for example, in Dall'Acqua et al., *J Immunol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present invention also contemplates additional modifications to an antibody or antigen binding site comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Protein Production

In one example, an antigen binding site described herein according to any example is produced by culturing a hybridoma under conditions sufficient to produce the protein, e.g., as described herein and/or as is known in the art.

Recombinant Expression

In another example, an antigen binding site described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. Nos. 4,816,567 or 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where an antigen binding site is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The antigen binding site prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Assaying Activity of an Antigen Binding Site

Binding to CXCR2 and Mutants Thereof

It will be apparent to the skilled artisan from the disclosure herein that antigen binding sites of the present invention bind to CXCR2. Methods for assessing binding to a protein are known in the art, e.g., as described in Scopes (In: Protein purification: principles and practice, Third Edition, Springer Verlag, 1994). Such a method generally involves immobilizing the antigen binding site and contacting it with labeled antigen (CXCR2). Following washing to remove non-specific bound protein, the amount of label and, as a consequence, bound antigen is detected. Of course, the antigen binding site can be labeled and the antigen immobilized. Panning-type assays can also be used. Alternatively, or additionally, surface plasmon resonance assays can be used.

Optionally, the dissociation constant (Kd), association constant (Ka) and/or affinity constant ($K_D$) of an immobilized antigen binding site for CXCR2 or an epitope thereof is determined. The "Kd" or "Ka" or "$K_D$" for an CXCR2-binding protein is in one example measured by a radiolabeled or fluorescently-labeled CXCR2 ligand binding assay. In the case of a "Kd", this assay equilibrates the antigen binding site with a minimal concentration of labeled CXCR2 or epitope thereof in the presence of a titration series of unlabeled CXCR2. Following washing to remove unbound CXCR2 or epitope thereof, the amount of label is determined, which is indicative of the Kd of the protein.

According to another example the Kd, Ka or $K_D$ is measured by using surface plasmon resonance assays, e.g., using BIAcore surface plasmon resonance (BIAcore, Inc., Piscataway, N.J.) with immobilized CXCR2 or a region thereof or immobilized antigen binding site.

Determining Inhibitory Activity

In some examples of the present invention, a protein is capable of inhibiting CXCR2 activity.

Various assays are known in the art for assessing the ability of a protein to inhibit or reduce signaling of a ligand through a receptor leading to a functional response.

In one example, the antigen binding site inhibits migration of immune cells (e.g., neutrophil cells) expressing CXCR2 which are cultured in the presence of a CXCR2 ligand (e.g. CXCL1, CXCL2, CXCL3, CXCL5 or CXCL6). Methods for assessing migration are known in the art and described herein. An antigen binding site that inhibits migration compared to the level observed in the absence of the antigen binding site is considered to inhibit or reduce CXCR2 activity, specifically CXCR2 mediated signalling and migration. Other assays to determine inhibitory activity of the anti-CXCR2 antibodies include calcium flux assay, radioligand binding assay, cAMP assay and beta arrestin recruitment assay. Any of the assays described herein may include one or more CXCR2 ligands including CXCL1, CXCL2, CXCL3, CXCL5 or CXCL6.

Assessing Therapeutic Efficacy

Assays for assessing therapeutic efficacy are described hereinabove in relation to determining neutralization by an antigen binding site.

Exemplary in vivo assays to test the CXCR2 inhibitory activity of the antibodies described herein include imiquimod induced skin inflammation model, K/B×N serum transfer induced arthritis, and B16 melanoma syngeneic model.

For example, the antigen binding site can be tested in a model of cancer, e.g., gastric cancer. For example, mice homologous for the Y757F mutant of gp130 ($gp130^{Y757F/Y757F}$) develop gastric tumors Jenkins et al, Blood 109: 2380-2388, 2007). Mice (e.g., eight week old mice) are treated with an antigen binding site and the number and/or weight of gastric polyps assessed. An antigen binding site that reduces polyp size and/or weight is considered useful for treating cancer. A similar assay can be used to test for an effect on colon cancer, in which $gp130^{Y757F/Y757F}$ mice are treated with azoxymethane (AOM) followed by dextran sodium sulfate (DSS) essentially as described in Greten (et al, Cell, 118: 285-296, 2004) to induce colon cancer prior to treatment with the antigen binding site.

The antigen binding site can additionally or alternatively be tested in a model of cancer metastasis or cancer-related bone disease, e.g., as described in Li et al., Oncol. Lett. 3: 802-806, 2012.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer, inflammatory disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophagelike synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

Conditions to be Treated

The antigen binding sites of the present invention are useful in the treatment or prevention of any condition associated, or caused by, the presence or over-expression of CXCR2. An example of a condition is cancer. Exemplary cancers include cystic and solid tumors, bone and soft tissue tumors, including tumors in anal tissue, bile duct, bladder, blood cells, bowel, brain, breast, carcinoid, cervix, eye, esophagus, head and neck, kidney, larynx, leukemia, liver, lung, lymph nodes, lymphoma, melanoma, mesothelioma, myeloma, ovary, pancreas, penis, prostate, skin (e.g. squamous cell carcinoma), sarcomas, stomach, testes, thyroid, vagina, vulva. Soft tissue tumors include Benign schwannoma Monosomy, Desmoid tumor, lipo-blastoma, lipoma, uterine leiomyoma, clear cell sarcoma, dermatofibrosarcoma, Ewing sarcoma, extraskeletal myxoid chondrosarcoma, liposarcooma myxoid, Alveolar rhabdomyosarcoma and synovial sarcoma. Specific bone tumors include nonossifying fibroma, unicameral bone cyst, enchon-droma, aneurismal bone cyst, osteoblastoma, chondroblastoma, chondromyxofibroma, ossifying fibroma and adamantinoma, Giant cell tumor, fibrous dysplasia, Ewing's sarcoma eosinophilic granuloma, osteosarcoma, chondroma, chondrosarcoma, malignant fibrous histiocytoma and metastatic carcinoma. Leukemias include acute lymphoblastic, acute myeloblastic, chronic lymphocytic and chronic myeloid.

Other examples include breast tumors, colorectal tumors, adenocarcinomas, mesothelioma, bladder tumors, prostate tumors, germ cell tumor, hepatoma/cholongio, carcinoma, neuroendocrine tumors, pituitary neoplasm, small 20 round cell tumor, squamous cell cancer, melanoma, atypical fibroxanthoma, seminomas, nonseminomas, stromal leydig cell tumors, Sertoli cell tumors, skin tumors, kidney tumors, testicular tumors, brain tumors, ovarian tumors, stomach tumors, oral tumors, bladder tumors, bone tumors, cervical tumors, esophageal tumors, laryngeal tumors, liver tumors, lung tumors, vaginal tumors and Wilm's tumor.

The antigen binding sites of the present invention are useful in the treatment or prevention of any condition associated, or caused by acute or chronic inflammation such as chronic obstructive pulmonary disease, asthma, fibrosis, psoriasis, colitis, type 1 diabetes, multiple sclerosis, sepsis, cystic fibrosis, arthritis, rheumatoid arthritis, inflammatory bowel disease, cystitis, and transplant rejection. The antigen binding site preferably find application in the treatment or prevention of autoimmune inflammatory conditions.

The antigen binding sites of the present invention are also useful as an allergy immunotherapy for the treatment of for example, allergic rhinitis, hay fever and bronchial asthma.

CXCL3 and 6 are chemoattractant for neutrophils during inflammation therefore they have a strong involvement in a wide range of inflammatory disorders. CXCL3 is overexpressed in breast cancer metastasis and prostate cancer. CXCL6 is involved in cystic fibrosis, promotes hepatocarcinoma cell proliferation and lung fibrosis. Accordingly, the antigen binding sites of the present invention find application in treating such disorders.

"Patient" or "subject in need thereof" refers to a living organism suffering from or prone to a disease or condition that can be treated by administration of a composition or pharmaceutical composition as provided herein. Non limiting examples include humans, other mammals, bovines, rats, mice, dogs, monkeys, goat, sheep, cows, deer, and other non mammalian animals. In some embodiments, a patient is human.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

The term "associated" or "associated with" in the context of a substance or substance activity or function associated with a disease (e.g., cancer (e.g. leukemia, acute myeloid leukemia)) means that the disease (e.g., cancer (e.g. leukemia, acute myeloid leukemia)) is caused by (in whole or in part), or a symptom of the disease is caused by (in whole or in part) the substance or substance activity or function. Alternatively, the substance (e.g., IL1RAP) may be an indicator of the disease (e.g., cancer (e.g. leukemia, acute myeloid leukemia)). Thus, an associated substance may serve as a means of targeting disease tissue (e.g., cancer cells (e.g., leukemia stem cells, acute myeloid leukemia cells))

Compositions

In some examples, an antigen binding site as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing an antigen binding site into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this invention are particularly useful for parenteral administration, such as intravenous administration or administration into a body cavity or lumen of an organ or joint. The compositions for administration will commonly comprise a solution of an antigen binding site dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of an antigen binding site of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, an antigen binding site of the present invention will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver an antigen binding site of the present invention.

WO2002/080967 describes compositions and methods for administering aerosolized compositions comprising antibodies for the treatment of, e.g., asthma, which are also suitable for administration of an antigen binding site of the present invention.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Dosages and Timing of Administration

Suitable dosages of an antigen binding site of the present invention will vary depending on the specific an antigen binding site, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present invention comprises administering a prophylactically or therapeutically effective amount of a protein described herein.

The term "therapeutically effective dose or amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). A person skilled in the art will be able to determine appropriate dosages depending on these and other factors. Accordingly, this term is not to be construed to limit the present invention to a specific quantity, e.g., weight or amount of protein(s), rather the present invention encompasses any amount of the antigen binding site(s) sufficient to achieve the stated result in a subject. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific antigen binding site(s) administered and/or the particular subject and/or the type or severity or level of condition and/or predisposition (genetic or otherwise) to the condition. Accordingly, this term is not to be construed to limit the present invention to a specific quantity, e.g., weight or amount of antigen binding site(s), rather the present invention encompasses any amount of the antigen binding site(s) sufficient to achieve the stated result in a subject.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Kits

The present invention additionally comprises a kit comprising one or more of the following:
(i) an antigen binding site of the invention or expression construct(s) encoding same;
(ii) a cell of the invention;
(iii) a complex of the invention; or
(iii) a pharmaceutical composition of the invention.

In the case of a kit for detecting CXCR2, the kit can additionally comprise a detection means, e.g., linked to a antigen binding site of the invention.

In the case of a kit for therapeutic/prophylactic use, the kit can additionally comprise a pharmaceutically acceptable carrier.

Optionally a kit of the invention is packaged with instructions for use in a method described herein according to any example.

TABLE 1

Summary of amino acid and nucleotide sequences

| ID No. | | SEQ ID NO: | Amino acid or nucleotide sequence |
|---|---|---|---|
| m3H9 | LCDR1 | 1 | QSLVHSNGNTY |
| | LCDR2 | 2 | KVS |
| | LCDR3 | 3 | SQGTHVPYT |
| | HCDR1 | 4 | GYAFSNSW |
| | HCDR2 | 5 | IYPGDGNI |
| | HCDR3 | 6 | ARSFLYVDFDY |
| | VL | 7 | VIVMTQTPLSLPVSLGDQASISCRSSQSLVH |
| | | | SNGNTYLQWYLQKPGQSPKLLIYKVSNRFS |
| | | | GVPDRFSGSGSGTDFTLKISRVEAEDLGVY |
| | | | FCSQGTHVPYTFGGGTKLEIKR |
| | VH | 8 | QVQLQQSGPELVKPGASVKISCKASGYAFS |
| | | | NSWMNWVKQRPGKGLEWIGRIYPGDGNIN |
| | | | YYGKFKDKATLTADKSSNTAYMQLSSLTSE |
| | | | DSAVYFCARSFLYVDFDYWGQGTTLTVSS |
| | VL (DNA) | 9 | GTTATTGTGATGACCCAAACTCCACTCTCCCTGCCTGTCA |
| | | | GTCTTGGAGATCAAGCCTCCATCTCTTGCAGATCTAGTCA |
| | | | GAGCCTTGTACACAGTAATGGAAACACCTATTTACAATG |
| | | | GTATCTGCAGAAGCCAGGCCAGTCTCCAAAGCTCCTGAT |
| | | | CTACAAAGTTTCCAACCGATTTTCTGGGGTCCCAGACAGG |
| | | | TTCAGTGGCAGTGGATCAGGGACAGATTTCACACTCAAG |
| | | | ATCAGCAGAGTGGAGGCTGAGGATCTGGGAGTTTATTTC |
| | | | TGCTCTCAAGGTACACATGTTCCGTACACGTTCGGAGGGG |
| | | | GGACCAAGCTGGAAATAAAACGG |

TABLE 1-continued

Summary of amino acid and nucleotide sequences

| ID No. | | SEQ ID NO: | Amino acid or nucleotide sequence |
|---|---|---|---|
| | VH (DNA) | 10 | CAGGTTCAGCTGCAGCAGTCTGGACCTGAGCTGGTGAAG CCTGGGGCCTCAGTGAAGATTTCCTGCAAGGCTTCTGGCT ACGCATTCAGTAACTCCTGGATGAACTGGGTGAAGCAGA GGCCTGGAAAGGGTCTTGAGTGGATTGGACGGATTTATC CTGGAGATGGAAATATTAACTACTATGGGAAGTTCAAGG ACAAGGCCACACTGACTGCAGACAAATCCTCCAACACAG CCTACATGCAACTCAGCAGCCTGACATCTGAGGACTCTGC GGTCTACTTCTGTGCAAGGAGTTTTCTCTACGTGGACTTT GACTACTGGGGCCAAGGCACCACTCTCACAGTCTCCTCA |
| m6G7 | LCDR1 | 11 | QTLVHSNGNTY |
| | LCDR2 | 12 | KVS |
| | LCDR3 | 13 | SQGTHVPYT |
| | HCDR1 | 14 | GYAFSNSW |
| | HCDR2 | 15 | IYPGDGNI |
| | HCDR3 | 16 | ARSFLYVDFDY |
| | VL | 17 | DVVMTQAPLSLPVSLGDQASISCRSSQTLV HSNGNTYLQWYLQKPGQSPKLLIYKVSNRF SGVPDRFSGSGSGTDFTLKISRVEAEDLGV YFCSQGTHVPYTFGGGTKLEIKR |
| | VH | 18 | QVQLQQSGPELVKPGASVKISCKASGYAFS NSWMNWVKQRPGKGLEWIGRIYPGDGNIN YYGKFKDKATLTADKSSNTAYMQLSSLTSE DSAVYFCARSFLYVDFDYWGQGTTLTVSS |
| | VL (DNA) | 19 | GATGTTGTGATGACCCAAGCTCCACTCTCCCTGCCTGTCA GTCTTGGAGATCAAGCCTCCATCTCTTGCAGGTCTAGTCA GACCCTTGTACACAGTAATGGAAACACCTATTTACAATG GTATCTGCAGAAGCCAGGCCAGTCTCCAAAGCTCCTGAT CTACAAAGTTTCCAACCGATTTTCTGGGGTCCCAGACAGG TTCAGTGGCAGTGGATCAGGGACAGATTTCACACTCAAG ATCAGCAGAGTGGAGGCTGAGGATCTGGGAGTTTATTTC TGCTCTCAAGGTACACATGTTCCGTACACGTTCGGAGGGG GGACCAAGCTGGAAATAAAACGG |
| | VH (DNA) | 20 | CAGGTTCAGCTGCAGCAGTCTGGACCTGAGCTGGTGAAG CCTGGGGCCTCAGTGAAGATTTCCTGCAAGGCTTCTGGCT ACGCATTCAGTAACTCCTGGATGAACTGGGTGAAGCAGA GGCCTGGAAAGGGTCTTGAGTGGATTGGACGGATTTATC CTGGAGATGGAAATATTAACTACTATGGGAAGTTCAAGG ACAAGGCCACACTGACTGCAGACAAATCCTCCAACACAG CCTACATGCAACTCAGCAGCCTGACATCTGAGGACTCTGC GGTCTACTTCTGTGCAAGGAGTTTTCTCTACGTGGACTTT GACTACTGGGGCCAAGGCACCACTCTCACAGTCTCCTCA |
| mCM2 | LCDR1 | 21 | QSLVHSNGNTY |
| | LCDR2 | 22 | KLS |
| | LCDR3 | 23 | SQSTHVPYT |
| | HCDR1 | 24 | GYAFSNSW |
| | HCDR2 | 25 | IYPGDGNI |
| | HCDR3 | 26 | ARSFLYVYFDY |
| | VL | 27 | DAVMTQTPLSLPVSLGDQASISCRSSQSLV HSNGNTYLQWYLQKPGQSPKLLIYKLSNRF SGVPDRFSGSGAGTDFTLKISRVEAEDLGV YFCSQSTHVPYTFGGGTKLEIKR |
| | VH | 28 | QVQLQQSGPELVKPGASVKISCKASGYAFS NSWMNWVKQRPGKGLEWIGRIYPGDGNIN YYGKFKDKATLTADKSSNTAYMQLSSLTSE DSAVYFCARSFLYVYFDYWGQGTTLTVSS |
| | VL (DNA) | 29 | GATGCGTGATGACCCAAACTCCACTCTCCCTGCCTGTCA GTCTTGGAGATCAAGCCTCCATCTCTTGCAGATCTAGTCA GAGCCTTGTACACAGTAATGGAAACACCTATTTACAATG GTATCTGCAGAAGCCAGGCCAGTCTCCAAAGCTCCTGAT CTACAAACTTTCCAACCGATTTTCTGGGGTCCCAGACAGG TTCAGTGGCAGTGGAGCAGGGACAGATTTCACACTCAAG ATCAGCAGAGTGGAGGCTGAGGATCTGGGAGTTTATTTC TGCTCTCAAAGTACACATGTTCCGTACACGTTCGGAGGGG GGACCAAGCTGGAAATAAAACGG |
| | VH (DNA) | 30 | CAGGTTCAGCTGCAGCAGTCTGGACCTGAACTGGTGAAG CCTGGGGCCTCAGTGAAGATTTCCTGTAAGGCTTCTGGCT ACGCATTCAGTAACTCCTGGATGAACTGGGTGAAGCAGA GGCCTGGAAAGGGTCTTGAGTGGATTGGACGGATTTATC CTGGAGATGGAAATATTAACTACTATGGGAAGTTCAAGG ACAAGGCCACACTGACTGCAGACAAATCCTCCAACACAG CCTACATGCAACTCAGCAGCCTGACATCTGAGGACTCTGC GGTCTACTTCTGTGCAAGGAGTTTTCTCTACGTGTACTTT GACTACTGGGGCCAAGGCACCACTCTCACAGTCTCCTCA |

TABLE 1-continued

Summary of amino acid and nucleotide sequences

| ID No. | | SEQ ID NO: | Amino acid or nucleotide sequence |
|---|---|---|---|
| h3H9 | LCDR1 | 1 | QSLVHSNGNTY |
| | LCDR2 | 2 | KVS |
| | LCDR3 | 3 | SQGTHVPYT |
| | HCDR1 | 4 | GYAFSNSW |
| | HCDR2 | 5 | IYPGDGNI |
| | HCDR3 | 6 | ARSFLYVDFDY |
| | VL | 31 | DIVMTQSPLSLPVTPGEPASISCRSSQSLVH SNGNTYLQWYLQKPGQSPQLLIYKVSNRFS GVPDRFSGSGSGTDFTLKISRVEAEDVGVY FCSQGTHVPYTFGQGTKLEIKR |
| | VH | 32 | QVQLVQSGAEVKKPGASVKVSCKASGYAF SNSWMNWVRQAPGQRLEWIGRIYPGDGNI NYYGKFKDKATLTADKSANTAYMELSSLR SEDTAVYFCARSFLYVDFDYWGQGTTLTVS S |
| m3H9 | LFR1 | 33 | VIVMTQTPLSLPVSLGDQASISCRSS |
| m6G7 | LFR1 | 34 | DVVMTQAPLSLPVSLGDQASISCRSS |
| mCM2 | LFR1 | 35 | DAVMTQTPLSLPVSLGDQASISCRSS |
| m3H9, m6G7 and mCM2 | LFR2 | 36 | LQWYLQKPGQSPKLLIY |
| m3H9 and m6G7 | LFR3 | 37 | NRFSGVPDRFSGSGSGTDFTLKISRVEAEDL GVYFC |
| mCM2 | LFR3 | 38 | NRFSGVPDRFSGSGAGTDFTLKISRVEAED LGVYFC |
| m3H9, m6G7 and mCM2 | LFR4 | 39 | FGGGTKLEIKR |
| m3H9, m6G7 and mCM2 | HFR1 | 40 | QVQLQQSGPELVKPGASVKISCKAS |
| m3H9, m6G7 and mCM2 | HFR2 | 41 | MNWVKQRPGKGLEWIGR |
| m3H9, m6G7 and mCM2 | HFR3 | 42 | NYYGKFKDKATLTADKSSNTAYMQLSSLT SEDSAVYFC |
| m3H9, m6G7 and mCM2 | HFR4 | 43 | WGQGTTLTVSS |
| h3H9 | LFR1 | 44 | DIVMTQSPLSLPVTPGEPASISCRSS |
| | LFR2 | 45 | LQWYLQKPGQSPQLLIY |
| | LFR3 | 46 | NRFSGVPDRFSGSGSGTDFTLKISRVEAED VGVYFC |
| | LFR4 | 47 | FGQGTKLEIKR |
| | HFR1 | 48 | QVQLVQSGAEVKKPGASVKVSCKAS |
| | HFR2 | 49 | MNWVRQAPGQRLEWIGR |
| | HFR3 | 50 | NYYGKFKDKATLTADKSANTAYMELSSLR SEDTAVYFC |
| | HFR4 | 51 | WGQGTTLTVSS |
| hCXCR2 | | 52 | MEDFNMESDSFEDFWKGEDLSNYSYSSTLPPFLLDAAPCEP ESLEINKYFVVIIYALVFLLSLLGNSLVMLVILYSRVGRSVTD VYLLNLALADLLFALTLPIWAASKVNGWIFGTFLCKVVSLL KEVNFYSGILLLACISVDRYLAIVHATRTLTQKRYLVKFICLS IWGLSLLLALPVLLFRRTVYSSNVSPACYEDMGNNTANWR |

TABLE 1-continued

Summary of amino acid and nucleotide sequences

| ID No. | | SEQ ID NO: | Amino acid or nucleotide sequence |
|---|---|---|---|
| | | | MLLRILPQSFGFIVPLLIMLFCYGFTLRTLFKAHMGQKHRAM<br>RVIFAVVLIFLLCWLPYNLVLLADTLMRTQVIQETCERRNHI<br>DRALDATEILGILHSCLNPLIYAFIGQKFRHGLLKILAIHGLIS<br>KDSLPKDSRPSFVGSSSGHTSTTL |
| | | 53 | MEDFNMESDSFEDFWKGEDLS |
| | | 54 | LSNYSYSSTLPPFLLDAAPCEPESLEINK |
| | | 55 | SFEDFWKGEDLSNYSYSSTLPP |
| h3H9 | mutated VH | 56 | QVQLVQSGAEVKKPGASVKVSCKASGYTFSNS<br>WMINWVRQAPGQRLEWIGRIYPGDGNINYYGK<br>FKDKATLTADKSANTAYMELSSLRSEDTAVYF<br>CARSFLYVDFDYWGQMILTVS |
| h3H9 | mutated VL | 57 | DIVMTQSPLSLPVTPGEPASISCRSSQSLVHSNG<br>NTYLQWYLQKPGESPQLLIYKVSNRFSGVPDRF<br>SGSGSGTDFTLKISRVEAEDVGVYFCSQGTHVP<br>YTFGQGTKLEIKR |
| h3H9 | mutated HCDR1 | 58 | GYTFSNSW |
| h3H9 | mutated LFR2 | 59 | LQWYLQKPGESPQUINT |
| | | 60 | SFEDFWKGEDLS |
| | | 61 | (Gly$_4$Ser)$_3$ |
| | | 62 | CPPC |

The present invention includes the following non-limiting Examples.

EXAMPLES

Example 1

Monoclonal antibodies reactive with human CXCR2 (hCXCR2) were generated by immunising C57BL/6 mice with 2×107 L1.2/hCXCR2 transfected cells stimulated 20 hours prior to harvest with 5 mM butyric acid and emulsified in Complete Freund's Adjuvant (1st immunization intraperitoneal) or Incomplete Freund's Adjuvant (2nd-6th immunizations intraperitoneal), for a total five to six times at 2-wk intervals. The final immunisation was injected intravenously in PBS. Four days later, the spleen was removed and cells were fused with the SP2/0 cell line using standard methods. Hybridomas were grown in DMEM (Gibco/Invitrogen) containing 10% Fetalclone (HyClone), 1×HAT supplement (Sigma Aldrich) plus mouse IL-6. After 10-14 days growth culture supernatant was taken for initial screening.

Monoclonal antibodies reactive with CXCR2 were identified using human CXCR2 transfected L1.2 cells, and untransfected L1.2 cells, or L1.2 cells transfected with unrelated or closely receptors such as hCXCRI, hCCR5 or hCXCR3 using immunofluorescent staining and analysis using a FACSCalibur (BD Biosciences). Monoclonal antibody staining of cells was performed using standard procedures as described previously (Lee et al., 2006, Nat. Biotech. 24:1279-1284).

Production of antibodies involved growing hybridomas in tissue culture flasks and harvesting the culture medium. For some experiments, the concentration of antibody in the culture supernatant was sufficient to proceed without further purification. Production of selected antibodies was scaled up and monoclonal antibodies were purified by protein G chromatography, concentrated and buffer exchanged into PBS. Monoclonal antibody concentration was determined using a total IgG ELISA.

L1.2 transfectants expressing high levels of hCXCR2 were used to immunize mice, and monoclonal antibodies were initially identified via flow cytometry that reacted with L1.2 cells transfected with hCXCR2. To ensure clonality, selected hybridomas were subcloned using dilution plating into a 384-well plate. The specificity of cross-reactivity of the subclones was confirmed by flow cytometry with L1.2/hCXCR2 transfectants and untransfected L1.2 cells.

Example 2

Receptor Binding Specificity

To assess reactivity of mAbs against transfected cells, we used indirect immunofluorescence staining and flow cytometry. Cells were washed once with PBS and resuspended in 100 µl PBS containing 2% (wt/vol) BSA and 0.1% (wt/vol) sodium azide (staining buffer) and purified antibody. After 30 min at 4° C., cells were washed twice with staining buffer and resuspended in 50 µl PE-conjugated anti-human IgG (Jackson ImmunoResearch Laboratories) diluted 1:500 in staining buffer for the detection of humanized mAbs or 50 µl PE-conjugated anti-mouse IgG (Jackson ImmunoResearch Laboratories) for the detection of mouse mAbs. After incubating for 20 min at 4° C., cells were washed twice with staining buffer and analyzed on LSRII flow cytometer. 7-AAD staining was used to exclude dead cells.

FIG. 1 shows the results of the flow cytometry experiments. All antibodies bound to cells expressing human CXCR2, however none of the antibodies showed any significant binding to human CCR6, CXCR1, CXCR3 or CXCR7 as the flow cytometry staining was identical to that observed with cells not expressing any chemokine receptor.

CXCR2 Binding Analysis

Figure 2:
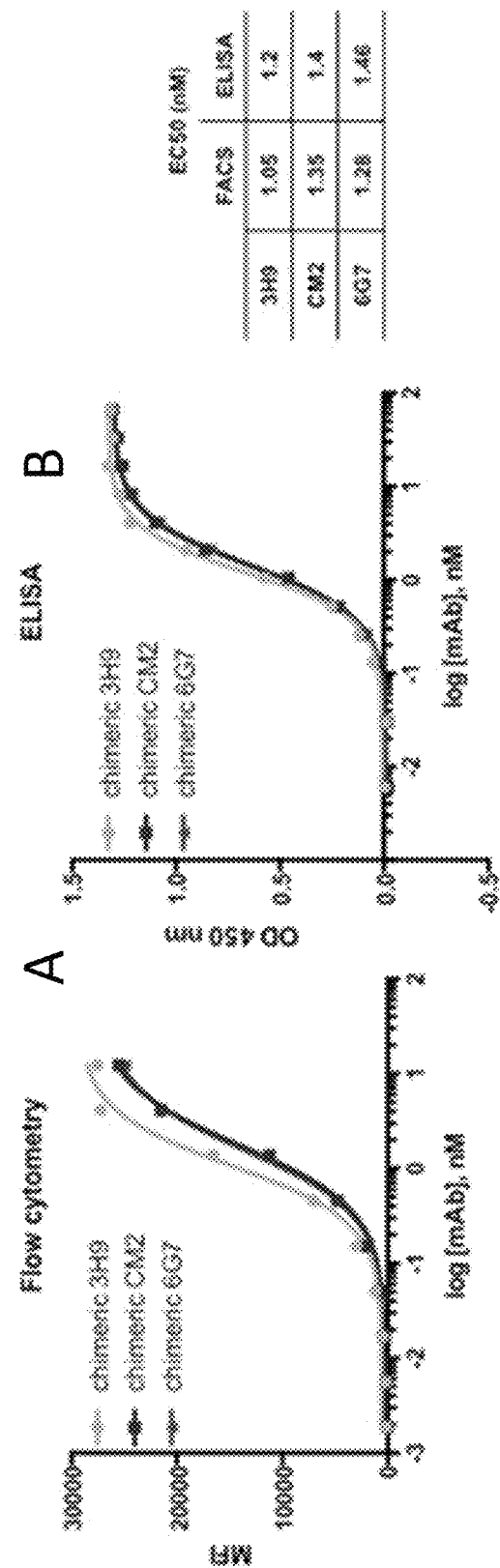
FIG. 2. CXCR2 receptor binding analysis. $EC_{50}$ for each of the antibodies binding to L1.2 hCXCR2 cells derived from flow cytometry (panel A) or ELISA experiments (panel B). $EC_{50}$ values from each type of binding assay correlated well and using flow cytometry the $EC_{50}$ values for 3H9, CM2 and 6G7 were 1.05 nM, 1.35 nM and 1.28 nM, respectively, whereas using an ELISA the $EC_{50}$ values for 3H9, CM2 and 6G7 were 1.2 nM, 1.4 nM and 1.46 nM, respectively.

FIG. 2 shows the $EC_{50}$ for each of the antibodies binding to L1.2 hCXCR2 cells derived from flow cytometry or ELISA experiments. $EC_{50}$ values from each type of binding assay correlated well and using flow cytometry the $EC_{50}$ values for 3H9, CM2 and 6G7 were 1.05 nM, 1.35 nM and 1.28 nM, respectively, whereas using an ELISA the $EC_{50}$ values for 3H9, CM2 and 6G7 were 1.2 nM, 1.4 nM and 1.46 nM, respectively.

Example 3

Competition Binding with CXCR2 Ligand

For ligand binding analysis, recombinant human GRO-g ("ligand") was obtained from Peprotech (New Jersey, USA). 125I-Bolton-Hunter-labelled GRO-g was purchased from Perkin-Elmer (Boston, Mass., USA), with a specific activity of 2200 Ci/mM. Cells were washed once in binding buffer (50 mM Hepes, pH 7.5, 1 mM CaCI, 5 mM MgCb, 0.5% BSA) and resuspended in binding buffer at a concentration of 2.5×106 cells/ml. Cold Purified monoclonal antibody (cold competitor) was added to a 96-well plate followed by an equal volume (40 µl) binding buffer containing 1×105 cells. Cells and competitor were preincubated at room temperature for 15 min. Then radiolabeled ligand (final concentration 0.5-2 nM) was added to each well to give a final reaction volume of 120 µl. After a 60-min incubation at room temperature, the cells were washed three times with 1 ml of binding buffer containing 150 mM NaCl. The radioactivity (amount of bound label) in the cell pellets was counted in a TopCount liquid scintillation counter (Packard). Non-specific background binding was calculated by incubating cells without radiolabelled-ligand. Samples were assayed in duplicate.

Figure 3:
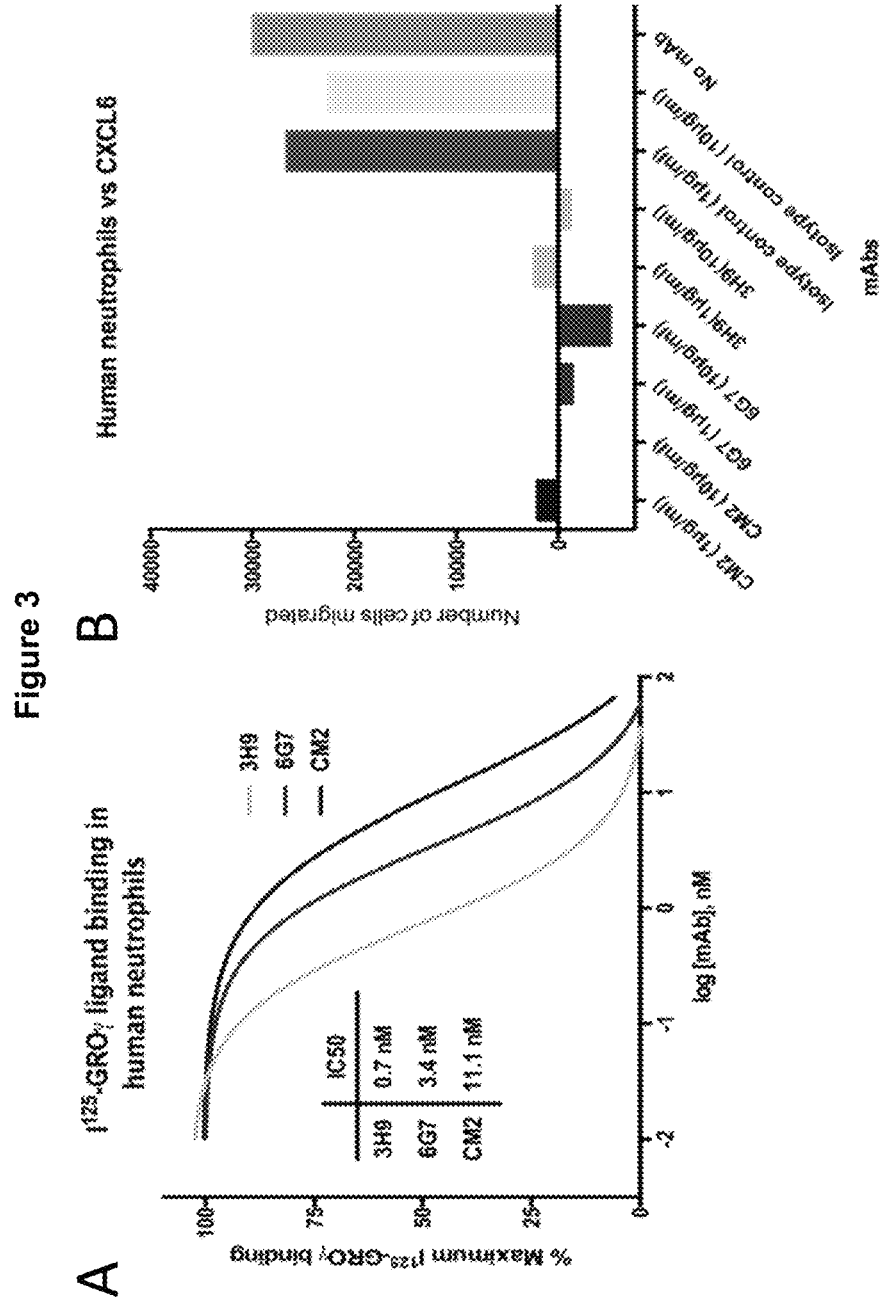
FIG. 3. Competition of antibodies with ligand for binding or activating CXCR2. Panel A of FIG. 3 shows that all antibodies compete with CXCL3 (Gro-γ; Gro-gamma) for binding to CXCR2 on human neutrophils. The $IC_{50}$ values for 3H9, 6G7 and CM2 are 0.7 nM, 3.4 nM and 11.1 nM, respectively. Panel B of FIG. 3 shows that all antibodies significantly inhibited neutrophil migration to the CXCR2 ligand CXCL6 (GCP-2) and all concentrations tested. The results of this experiment clearly show that all antibodies can potently inhibit CXCR2 mediated function.

FIG. 3A shows that all antibodies compete with CXCL3 (Gro-γ; Gro-gamma) for binding to CXCR2 on human neutrophils. The $IC_{50}$ values for 3H9, 6G7 and CM2 are 0.7 nM, 3.4 nM and 11.1 nM, respectively. Surprisingly, 3H9 exhibited a sub-nanomolar $IC_{50}$ value.

Inhibition of Neutrophil Migration

Human neutrophils were spun down and washed in migration medium (MM=RPMI 1640, 0.5% BSA) and resuspended at $10^7$ cells/ml. Tissue culture inserts (Becton Dickinson & Co., Mountain View, Calif.) were placed in each of the wells of 24-well tissue-culture plates, forming an upper and lower chamber separated by a polyethylene terepthalate membrane bearing 3-mm-diameter pores. Chemotactic CXCL6 (diluted in assay medium) was added to 600 µl of assay medium in the 24-well tissue culture plates. One million cells in 100 µl were pre-incubated for 30 mins with the antibodies. The purified mAb was added to the upper chamber in the wells and the cells were allowed to migrate through to the lower chamber in an 5% CO2, 37° C. incubator for 4 h. The inserts were removed after migration and the cells were counted by the LSRII cytometer (BD Biosciences). Relative cell counts were obtained by acquiring events for a set time period of 30 seconds.

FIG. 3B shows that all antibodies significantly inhibited neutrophil migration to the CXCR2 ligand CXCL6 (GCP-2) and all concentrations tested. The results of this experiment clearly show that all antibodies can potently inhibit CXCR2 mediated function.

Figure 7:
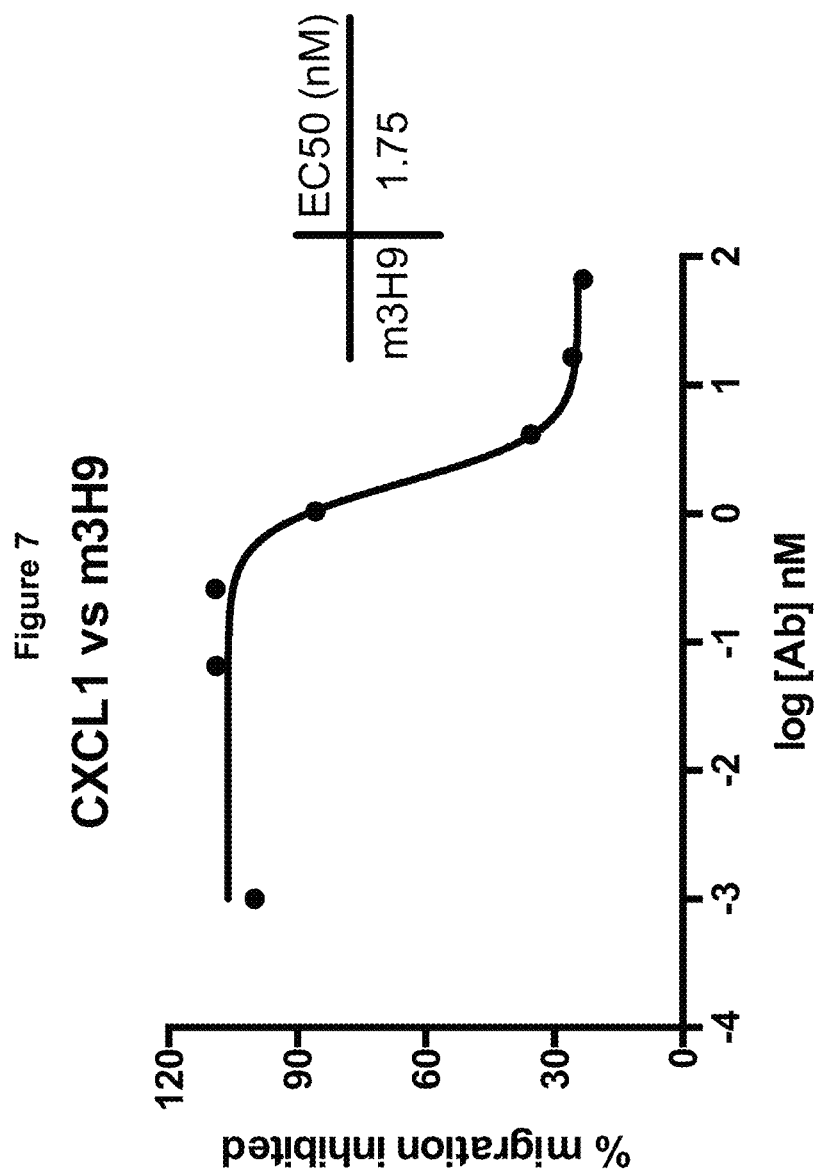
FIG. 7. Purified mouse 3H9 mAb inhibited CXCL1-induced migration of human neutrophils.
Figure 8:
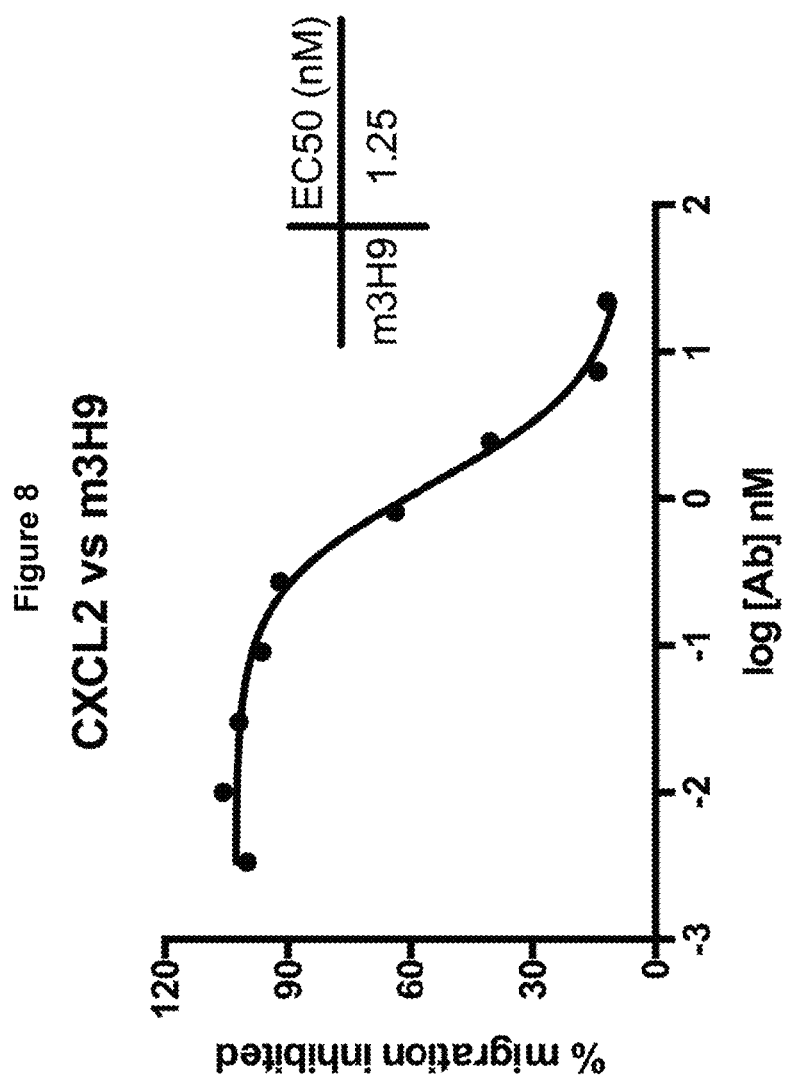
FIG. 8. Purified mouse 3H9 mAb inhibited CXCL2-induced migration of human neutrophils.
Figure 9:
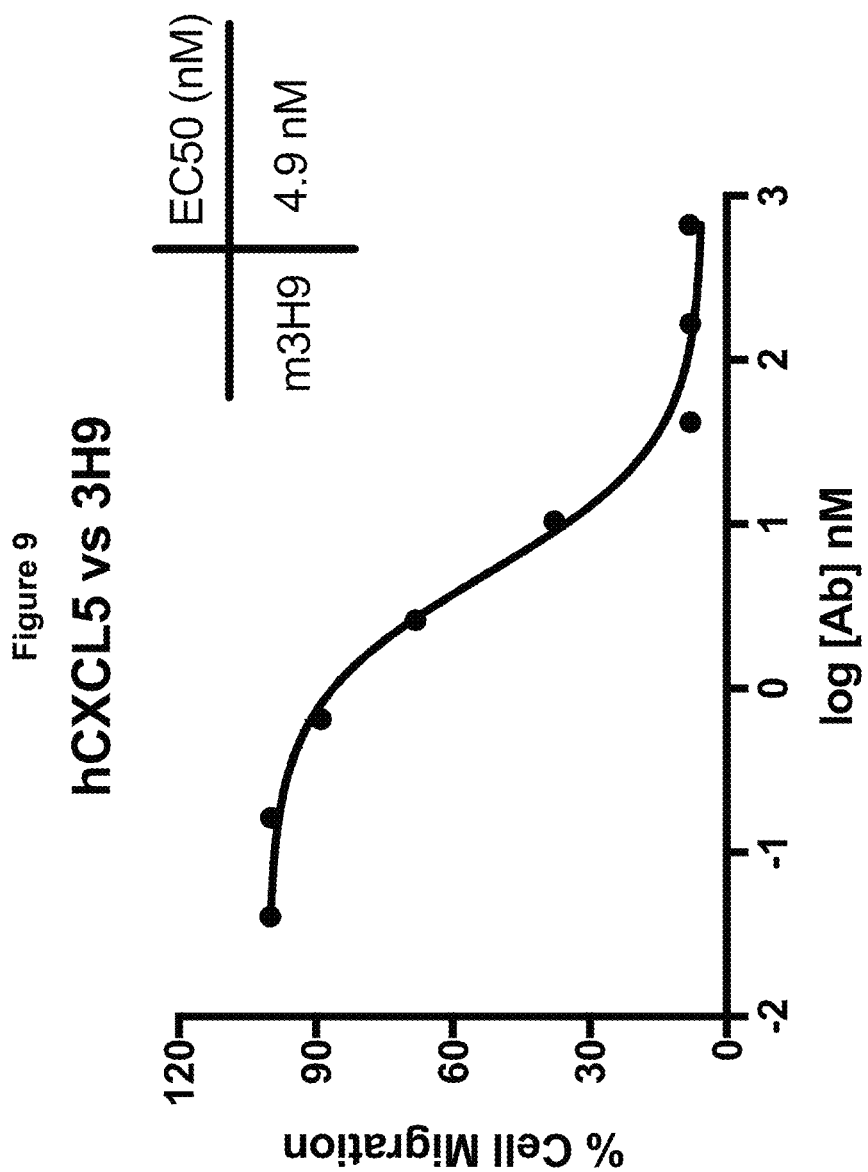
FIG. 9. Purified mouse 3H9 mAb inhibited hCXCL5-induced migration of human neutrophils.
Figure 10:
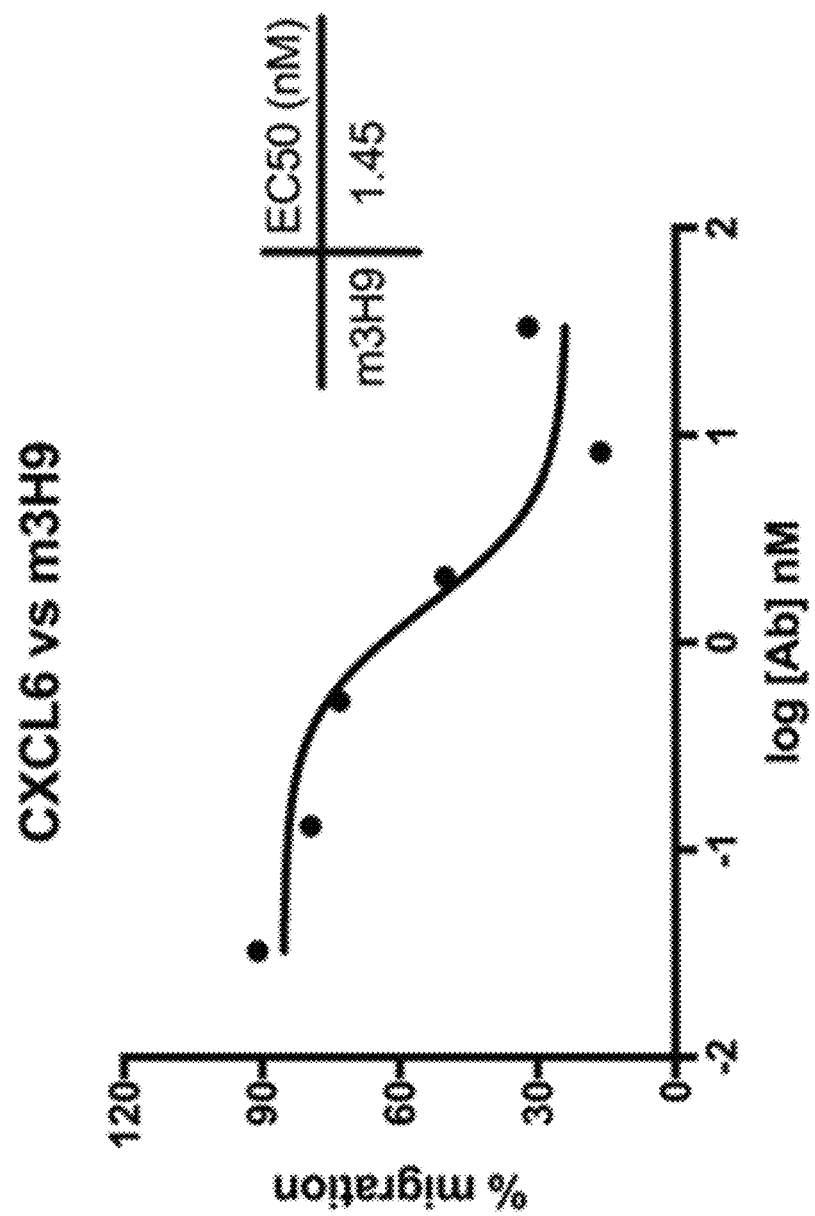
FIG. 10. Purified mouse 3H9 mAb inhibited CXCL6-induced migration of human neutrophils.

Further, FIGS. 7, 8 and 9 also show that an anti-CXCR2 antibody can potently inhibit CXCL1, CXCL2, CXCL5-induced migration of human neutrophils, respectively.

Example 4

Epitope Mapping Analysis

Epitope mapping studies were performed to determine the region within CXCR2 that is recognized by anti-CXCR2 mAb. Initially, biotinylated peptides corresponding to the N-terminal region and the first, second and third extracellular loops of human CXCR2 were used in an ELISA. The results of this preliminary mapping study indicated that all the anti-human CXCR2 mAb recognized the N-terminal region of CXCR2.

Three overlapping biotinylated peptides spanning the entire N-terminal region of human CXCR2 were then synthesized and used in more defined anti-CXCR2 mAb epitope mapping studies. Peptide 1 (MEDFN-MESDSFEDFWKGEDLS) (SEQ ID NO:53) corresponds to amino acid position 1-21 of the human CXCR2; Peptide 2 (SFEDFWKGEDLSNYSYSSTLPP) (SEQ ID NO:55) corresponds to amino acid position 10-31 and Peptide 3 (LSNY-SYSSTLPPFLLDAAPCEPESLEINK) (SEQ ID NO:54) corresponds to amino acid 20-46 position of the human CXCR2. Briefly, multiwell plates were coated with streptavidin and washed before the biotinylated peptides were added to separate wells and incubated to facilitate binding of the peptides to the plate. Different anti-human CXCR2 antibodies were then tested by adding the respective antibodies to the wells of the plate and incubating the plate. An isotype control and buffer only were included as negative controls. Following washing, appropriate conjugated antibodies were added and the plates were incubated. The plates were washed again and binding of the antibodies to the immobilised peptides was visualised.

Figure 4:
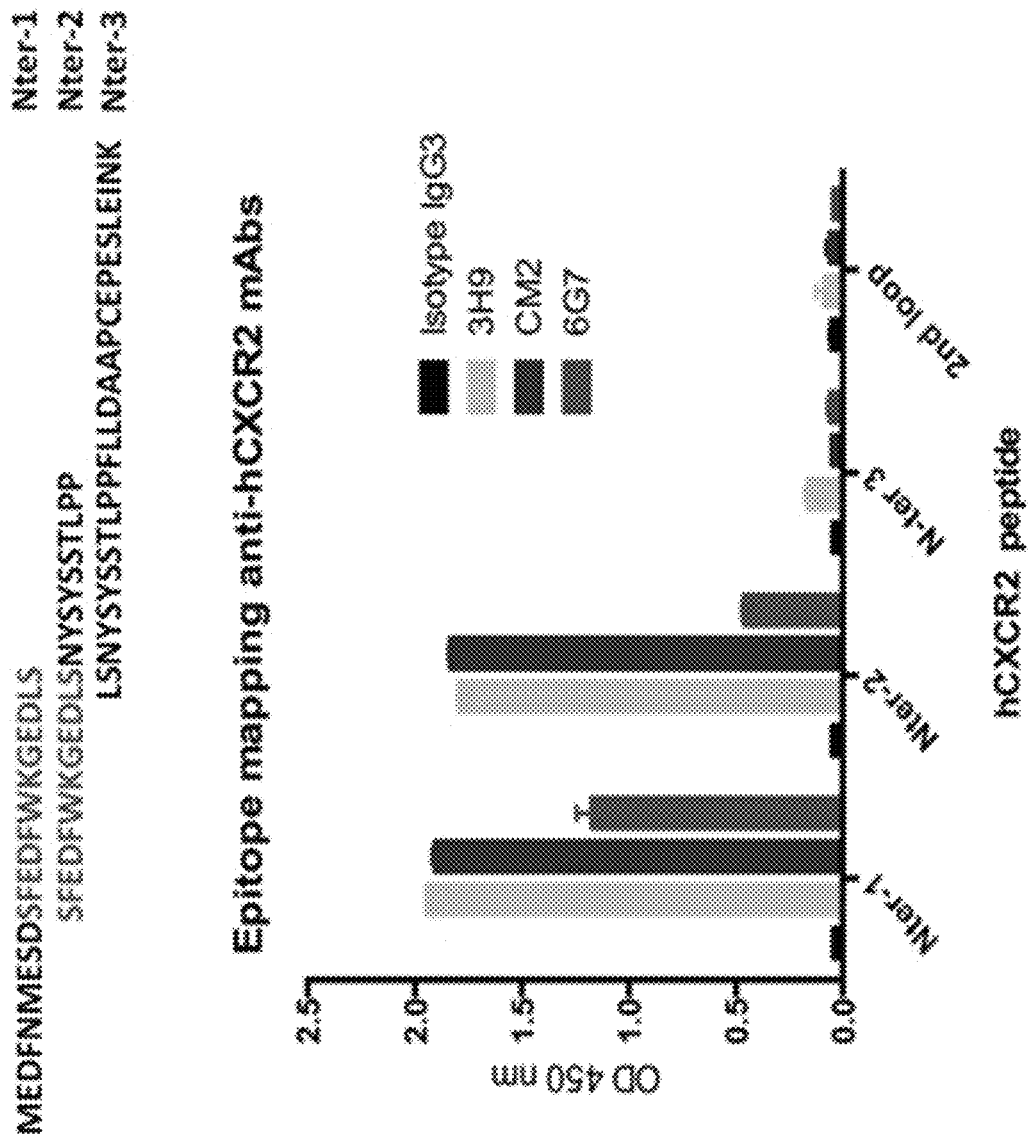
FIG. 4. Epitope mapping. Three overlapping biotinylated peptides spanning the entire N-terminal region of human CXCR2 were then synthesized and used in more defined anti-CXCR2 mAb epitope mapping studies. Peptide 1/Nter-1 (MEDFNMESDSFEDFWKGEDLS) (SEQ ID NO:53) corresponds to amino acid position 1-21 of the human CXCR2; Peptide 2/Nter-2 (SFEDFWKGEDLSNY-SYSSTLPP) (SEQ ID NO:55) corresponds to amino acid position 10-31 and Peptide 3/Nter-3 (LSNYSYSSTLPP-FLLDAAPCEPESLEINK) (SEQ ID NO:54) corresponds to amino acid 20-46 position of the human CXCR2. No binding was observed for isotype control to any peptide, nor any of the antibodies tested to peptide 3 or $2^{nd}$ loop. Binding of 3H9, CM2 and 6G7 was observed for peptides 1 and 2.

FIG. 4 shows that antibodies 3H9, CM2 and 6G7 all bind to peptides 1 and 2, but do not bind to peptide 3. Consequently, the region or epitope on CXCR2 that is involved in antibody binding is SFEDFWKGEDLS (SEQ ID NO:60) or amino acids 10 to 21 (numbering as per human CXCR2).

Example 5

Humanisation of Anti-CXCR2 Antibody

Total RNA from the anti-hCXCR2 hybridoma 3H9 was used to synthesize cDNA for sequencing analysis. The variable region genes were amplified by RT-PCR using primers annealing to the mouse light (mIgCk) and heavy (mIgG3) constant regions, and the variable heavy chain (VH) and variable light chain (VL) genes were sequenced.

Humanized 3H9 mAb was generated by transferring the CDRs of the m3H9 mAb (CDR-H1; CDR-H2; CDR-H3; CDR-L1; CDR-L2; and CDR-L3) onto human framework regions using standard molecular techniques. IMGT/V-QUEST and IMGT/Junctions analysis tools were used to identify human germline genes in which sequences from the variable regions of both the heavy and light chains were closely aligned with those of murine antibody. Framework sequences of these selected human germline genes were used as acceptor sequences for the mouse 3H9 CDRs (IGHV1-3*01 and IGKV2-28*01 human genes according to IMGT database). However, murine residues were retained in the critical "Vernier" zone. The humanized VH and VL genes, which were also codon optimized for expressed in CHO cells, were synthesized by Genescript.

To assess reactivity of humanized mAb against transfected cells, we used indirect immunofluorescence staining and flow cytometry. Cells were washed once with PBS and resuspended in 100 µl PBS containing 2% (wt/vol) BSA and 0.1% (wt/vol) sodium azide (staining buffer) and 1 ug of purified chimeric 3H9 or humanized 3H9. After 30 min at 4° C., cells were washed twice with staining buffer and resuspended in 50 µl PE-conjugated anti-human IgG (Jackson ImmunoResearch Laboratories) diluted 1:500 in staining buffer for the detection of humanized mAbs (Jackson ImmunoResearch Laboratories) for the detection of mouse mAbs. After incubating for 20 min at 4° C., cells were washed twice with staining buffer and analyzed on LSRII flow cytometer. 7-AAD staining was used to exclude dead cells.

Figure 5:
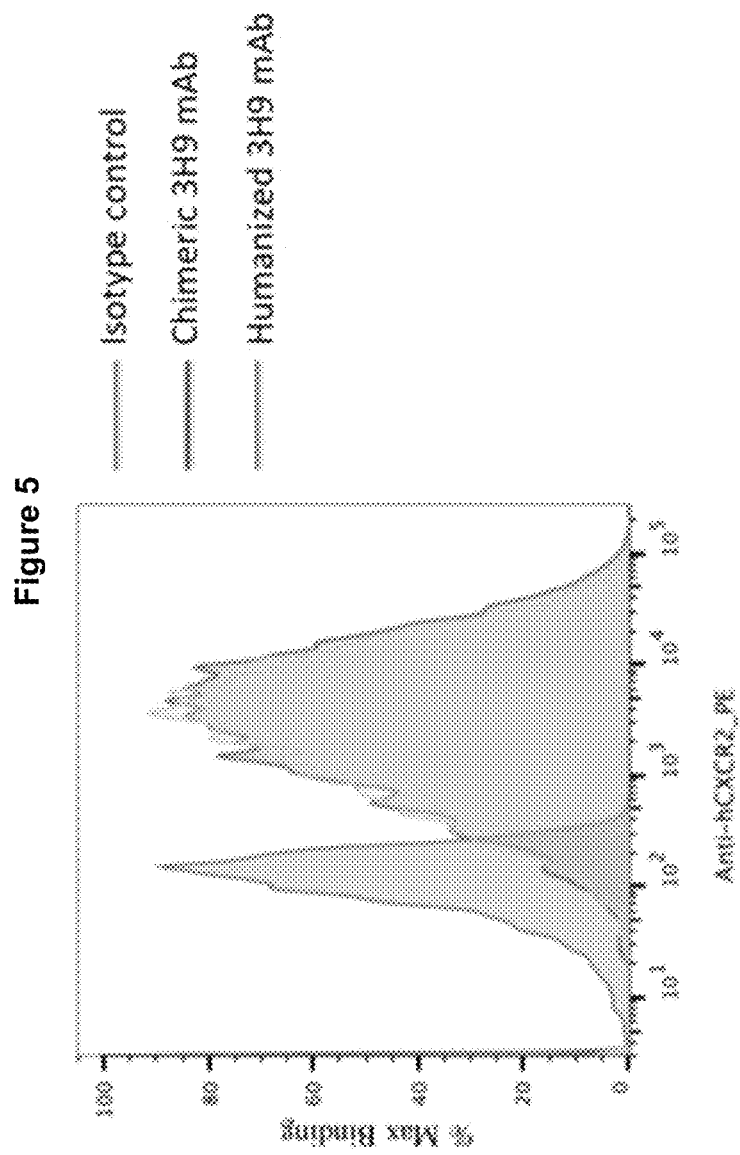
FIG. 5. CXCR2 receptor binding analysis of a humanised antibody. The results of flow cytometry binding analysis with the humanised 3H9 and the chimeric 3H9. Both antibodies bound to CXCR2 expressing cells to the same extent indicating that humanisation is unlikely to have resulted in any appreciable reduction in affinity for CXCR2.
Figure 6:
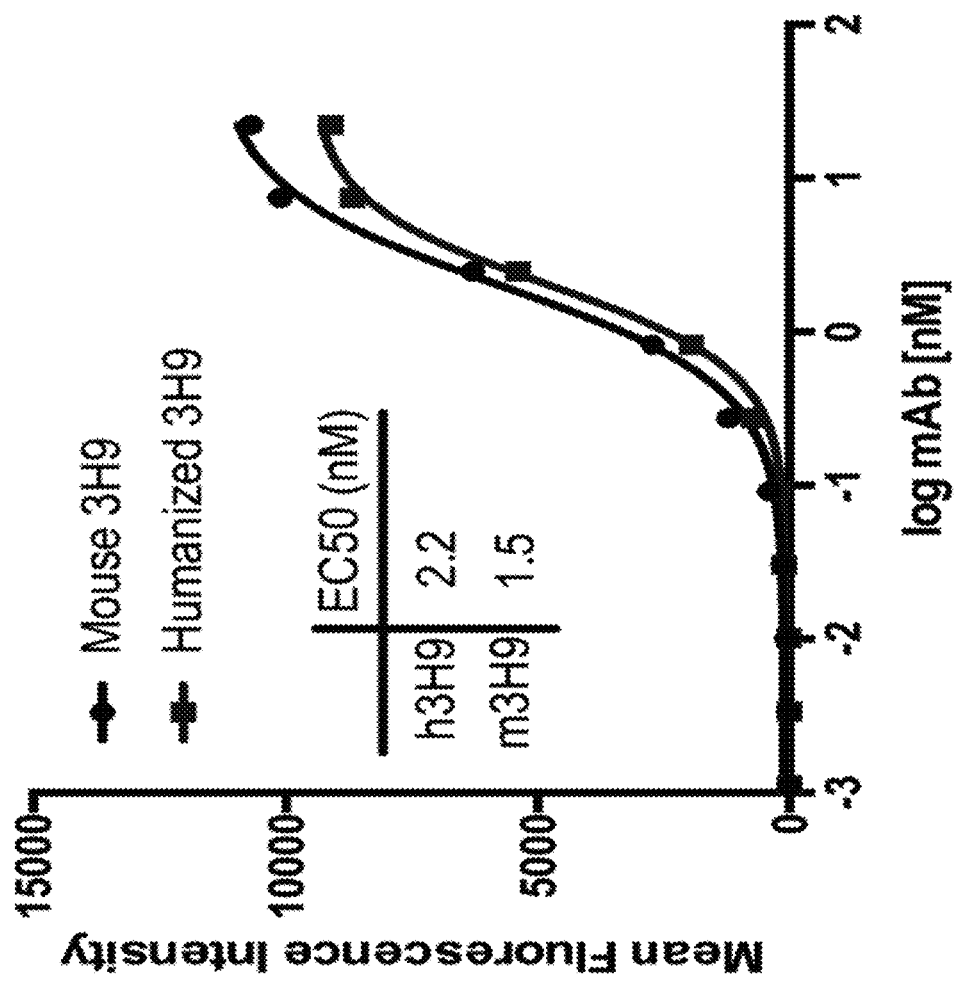
FIG. 6. Purified mouse 3H9 and humanized 3H9 dose response binding to human CXCR2 L1.2 transfected cells by flow cytometry.

FIG. 5 shows the results of flow cytometry binding analysis with the humanised 3H9 and the chimeric 3H9. Both antibodies bound to CXCR2 expressing cells to the same extent indicating that humanisation is unlikely to have resulted in any appreciable reduction in affinity for CXCR2. This was confirmed with the results shown in FIG. 6 where the mouse and humanised 3H9 had similar $EC_{50}$ values for binding to CXCR2 L1.2 transfected cells.

It will be understood that the invention disclosed and defined in this specification extends to all alternative combinations of two or more of the individual features mentioned or evident from the text or drawings. All of these different combinations constitute various alternative aspects of the invention.

P EMBODIMENTS

P Embodiment 1

An antigen binding site that binds to CXCR2 and inhibits CXCL2, CXCL3 and/or CXCL6 mediated CXCR2 activity.

P Embodiment 2

An antigen binding site according to P embodiment 1, wherein the antigen binding site does not detectably bind to or bind significantly to CCR6, CXCR1, CXCR2 and/or CXCR7.

P Embodiment 3

An antigen binding site according to P embodiment 1 or 2, wherein the antigen binding site inhibits or reduces CXCR2 activity induced by CXCL2, CXCL3 and CXCL6.

P Embodiment 4

An antigen binding site according to P embodiment 1 or 2, wherein the antigen binding site competes with CXCL2, CXCL3 and/or CXCL6 for binding to CXCR2.

P Embodiment 5

An antigen binding site according to any one of P embodiments 1, 2 or 4, wherein the antigen binding site inhibits the migration of an immune cell stimulated by CXCL2, CXCL3 or CXCL6.

P Embodiment 6

An antigen binding site according to any one of P embodiments 1 to 5, wherein the antigen binding site exhibits an $EC_{50}$ of less than 2 nM for inhibiting CXCL2, CXCL3 and/or CXCL6 mediated CXCR2 activity.

P Embodiment 7

An antigen binding site according to P embodiment 4, wherein the antigen binding site exhibits an $IC_{50}$ in a competition binding assay with CXCL3 of less than about 20, 15, 12, 10, 8, 6, 5, 4, 3, 2, or 1 nM.

P Embodiment 8

An antigen binding site according to any one of P embodiments 1 to 7, wherein the antigen binding site further inhibits CXCL1 mediated CXCR2 activity.

P Embodiment 9

An antigen binding site according to any one of P embodiments 1 to 8, wherein the antigen binding site binds to an N-terminal region of CXCR2.

P Embodiment 10

An antigen binding site according to P embodiment 9, wherein the N-terminal region comprises or consists of residues 10 to 21 (numbering as per human CXCR2).

P Embodiment 11

An antigen binding site according to P embodiment 10, wherein residues 10 to 21 are SFEDFWKGEDLS (SEQ ID NO:60).

P Embodiment 12

An antigen binding site according to P embodiment 10 or 11, wherein the antigen binding site binds within residues 10 to 21 and no other residues within the first 46 residues of CXCR2.

P Embodiment 13

An antigen binding site according to any one of P embodiments 1 to 12, wherein the antigen binding site binds to a peptide consisting of the amino acid sequence of SEQ ID NO: 52 and a further peptide consisting of the amino acid sequence of SEQ ID NO: 53, but does not detectably bind to a peptide consisting of the amino acid sequence of SEQ ID NO: 54.

P Embodiment 14

An antigen binding site for binding to CXCR2, the antigen binding site comprising: FR1-CDR1-FR2-CDR2-FR3-CDR3-FR4-linker-FR1a-CDR1a-FR2a-CDR2a-FR3a-CDR3a-FR4a, wherein: FR1, FR2, FR3 and FR4 are each framework regions; CDR1, CDR2 and CDR3 are each complementarity determining regions; FR1a, FR2a, FR3a and FR4a are each framework regions; CDR1a, CDR2a and CDR3a are each complementarity determining regions; wherein the sequence of any of the framework regions or complementarity determining regions are as described herein.

P Embodiment 15

An antigen binding site for binding to CXCR2, the antigen binding site including: FR1-CDR1-FR2-CDR2-FR3-CDR3-FR4-linker-FR1a-CDR1a-FR2a-CDR2a-FR3a-CDR3a-FR4a wherein: FR1, FR2, FR3 and FR4 are each framework regions; CDR1, CDR2 and CDR3 are each complementarity determining regions; FR1a, FR2a, FR3a and FR4a are each framework regions; CDR1a, CDR2a and CDR3a are each complementarity determining regions; wherein the sequence of any of the complementarity determining regions have an amino acid sequence as described in Table 1 herein.

P Embodiment 16

An antigen binding site comprising, consisting essentially of or consisting of an amino acids sequence of (in order of N to C terminus or C to N terminus): —SEQ ID NO: 7 and 8; —SEQ ID NO: 17 and 18; —SEQ ID NO: 27 and 28; and/or —SEQ ID NO: 31 and 32.

P Embodiment 17

An antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:4, a CDR2 comprising a sequence at least about 80%, at least 85%, at least 90%, at least 92%, at least 95%, at least 97%, at least 99% identical to a sequence set in SEQ ID NO:5 and a CDR3 comprising a sequence at least about 80%, at least 85%, at least 90%, at least 92%, at least 95%, at least 97%, at least 99% identical to a sequence set forth in SEQ ID NO: 6;
(ii) a VH comprising a sequence at least about 95% or 96% or 97% or 98% or 99% identical to a sequence set forth in SEQ ID NO: 8 or 32;
(iii) a VL comprising a CDR1 comprising a sequence at least about 80%, at least 85%, at least 90%, at least 92%, at least 95%, at least 97%, at least 99% identical to a sequence set forth in SEQ ID NO: 1, a CDR2 comprising a sequence at least about 80%, at least 85%, at least 90%, at least 92%, at least 95%, at least 97%, at least 99% identical to a sequence set forth in SEQ ID NO: 2 and a CDR3 comprising a sequence at least about 80%, at least 85%, at least 90%, at least 92%, at least 95%, at least 97%, at least 99% identical to a sequence set forth in SEQ ID NO: 3;
(iv) a VL comprising a sequence at least about 95% identical to a sequence set forth in SEQ ID NO: 7 or 31;
(v) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6;
(vi) a VH comprising a sequence set forth in SEQ ID NO: 8 or 32;
(vii) a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3;
(viii) a VL comprising a sequence set forth in SEQ ID NO: 7 or 31;
(ix) a VH comprising a CDR1 comprising a sequence set forth in SEQ ID NO: 4, a CDR2 comprising a sequence set forth between in SEQ ID NO: 5 and a CDR3 comprising a sequence set forth in SEQ ID NO: 6; and a VL comprising a CDR1 comprising a sequence set SEQ ID NO: 1, a CDR2 comprising a sequence set forth in SEQ ID NO: 2 and a CDR3 comprising a sequence set forth in SEQ ID NO: 3;
(x) a VH comprising a sequence set forth in SEQ ID NO: 8 and a VL comprising a sequence set forth in SEQ ID NO: 7; or (xi) a VH comprising a sequence set forth in SEQ ID NO: 32 and a VL comprising a sequence set forth in SEQ ID NO: 31.

P Embodiment 18

An antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:14, a CDR2 comprising a sequence at least about 80%, at least 85%, at least 90%, at least 92%, at least 95%, at least 97%, at least 99% identical to a sequence set in SEQ ID NO:15 and a CDR3 comprising a sequence at least about 80%, at least 85%, at least 90%, at least 92%, at least 95%, at least 97%, at least 99% identical to a sequence set forth in SEQ ID NO: 16;
(ii) a VH comprising a sequence at least about 95% or 96% or 97% or 98% or 99% identical to a sequence set forth in SEQ ID NO: 18;
(iii) a VL comprising a CDR1 comprising a sequence at least about 80%, at least 85%, at least 90%, at least 92%, at least 95%, at least 97%, at least 99% identical to a sequence set forth in SEQ ID NO: 11, a CDR2 comprising a sequence at least about 80%, at least 85%, at least 90%, at least 92%, at least 95%, at least 97%, at least 99% identical to a sequence set forth in SEQ ID NO: 12 and a CDR3 comprising a sequence at least about 80%, at least 85%, at least 90%, at least 92%, at least 95%, at least 97%, at least 99% identical to a sequence set forth in SEQ ID NO: 13;
(iv) a VL comprising a sequence at least about 95% identical to a sequence set forth in SEQ ID NO: 17;
(v) a VH comprising a CDR1 comprising a sequence set forth in SEQ ID NO: 14, a CDR2 comprising a sequence set forth between in SEQ ID NO: 15 and a CDR3 comprising a sequence set forth in SEQ ID NO: 16;
(vi) a VH comprising a sequence set forth in SEQ ID NO: 18;
(vii) a VL comprising a CDR1 comprising a sequence set SEQ ID NO: 11, a CDR2 comprising a sequence set forth in SEQ ID NO: 12 and a CDR3 comprising a sequence set forth in SEQ ID NO: 13;
(viii) a VL comprising a sequence set forth in SEQ ID NO: 17;
(ix) a VH comprising a CDR1 comprising a sequence set forth in SEQ ID NO: 14, a CDR2 comprising a sequence set forth between in SEQ ID NO: 15 and a CDR3 comprising a sequence set forth in SEQ ID NO: 16; and a VL comprising a CDR1 comprising a sequence set SEQ ID NO: 11, a CDR2 comprising a sequence set forth in SEQ ID NO: 12 and a CDR3 comprising a sequence set forth in SEQ ID NO: 13; or
(x) a VH comprising a sequence set forth in SEQ ID NO: 18 and a VL comprising a sequence set forth in SEQ ID NO: 17.

P Embodiment 19

An antigen binding site comprising an antigen binding domain of an antibody, wherein the antigen binding domain binds to or specifically binds to CXCR2, wherein the antigen binding domain comprises at least one of:
(i) a VH comprising a complementarity determining region (CDR) comprising a sequence at least about 80%, at least 85%, at least 90%, at least 92%, at least 95%, at least 97%, at least 99% identical to a sequence set forth in SEQ ID NO:24, a CDR2 comprising a sequence at least about 80%, at least 85%, at least 90%, at least 92%, at least 95%, at least 97%, at least 99% identical to a sequence set in SEQ ID NO: 25 and a CDR3 comprising a sequence at least about 80%, at least 85%, at least 90%, at least 92%, at least 95%, at least 97%, at least 99% identical to a sequence set forth in SEQ ID NO: 26;
(ii) a VH comprising a sequence at least about 95% or 96% or 97% or 98% or 99% identical to a sequence set forth in SEQ ID NO: 28;
(iii) a VL comprising a CDR1 comprising a sequence at least about 80%, at least 85%, at least 90%, at least 92%, at least 95%, at least 97%, at least 99% identical to a sequence set forth in SEQ ID NO: 21, a CDR2 comprising a sequence at least about 80%, at least 85%, at least 90%, at least 92%, at least 95%, at least 97%, at least 99% identical to a sequence set forth in SEQ ID NO: 22 and a CDR3 comprising a sequence at least about 80%, at least 85%, at least 90%, at least 92%, at least 95%, at least 97%, at least 99% identical to a sequence set forth in SEQ ID NO: 23;
(iv) a VL comprising a sequence at least about 95% identical to a sequence set forth in SEQ ID NO: 27;
(v) a VH comprising a CDR1 comprising a sequence set forth in SEQ ID NO: 24, a CDR2 comprising a sequence set forth between in SEQ ID NO: 25 and a CDR3 comprising a sequence set forth in SEQ ID NO: 26;
(vi) a VH comprising a sequence set forth in SEQ ID NO: 28;
(vii) a VL comprising a CDR1 comprising a sequence set SEQ ID NO: 21, a CDR2 comprising a sequence set forth in SEQ ID NO: 22 and a CDR3 comprising a sequence set forth in SEQ ID NO: 23;
(viii) a VL comprising a sequence set forth in SEQ ID NO: 27;
(ix) a VH comprising a CDR1 comprising a sequence set forth in SEQ ID NO: 24, a CDR2 comprising a sequence set forth between in SEQ ID NO: 25 and a CDR3 comprising a sequence set forth in SEQ ID NO: 26; and a VL comprising a CDR1 comprising a sequence set SEQ ID NO: 21, a CDR2 comprising a sequence set forth in SEQ ID NO: 22 and a CDR3 comprising a sequence set forth in SEQ ID NO: 23; or
(x) a VH comprising a sequence set forth in SEQ ID NO: 28 and a VL comprising a sequence set forth in SEQ ID NO: 27.

P Embodiment 20

An antigen binding according to any one of P embodiments 16 to 18, wherein the antigen binding domain further comprises at least one of:
(i) a VH comprising a framework region (FR) 1 comprising a sequence at least about 80%, at least 85%, at least 90%, at least 92%, at least 95%, at least 97%, at least 99% identical to a sequence set forth in SEQ ID NO:40 or 48, a FR2 comprising a sequence at least about 80%, at least 85%, at least 90%, at least 92%, at least 95%, at least 97%, at least 99% identical to a sequence set in SEQ ID NO:41 or 49, a FR3 comprising a sequence at least about 80%, at least 85%, at least 90%, at least 92%, at least 95%, at least 97%, at least 99% identical to a sequence set forth in SEQ ID NO: 42 or 50, and a FR4 comprising a sequence at least about 80%, at least 85%, at least 90%, at least 92%, at least 95%, at least 97%, at least 99% identical to a sequence set forth in SEQ ID NO: 43 or 51;

(ii) a VL comprising a FR1 comprising a sequence at least about 80%, at least 85%, at least 90%, at least 92%, at least 95%, at least 97%, at least 99% identical to a sequence set forth in SEQ ID NO: 33, 34, 35 or 44, a FR2 comprising a sequence at least about 80%, at least 85%, at least 90%, at least 92%, at least 95%, at least 97%, at least 99% identical to a sequence set forth in SEQ ID NO: 36 or 45, a FR3 comprising a sequence at least about 80%, at least 85%, at least 90%, at least 92%, at least 95%, at least 97%, at least 99% identical to a sequence set forth in SEQ ID NO: 37, 38 or 46, and a FR4 comprising a sequence at least about 80%, at least 85%, at least 90%, at least 92%, at least 95%, at least 97%, at least 99% identical to a sequence set forth in SEQ ID NO: 39 or 47;
(iii) a VH comprising a FR1 comprising a sequence set forth in SEQ ID NO: 40 or 48, a FR2 comprising a sequence set forth between in SEQ ID NO: 41 or 49, a FR3 comprising a sequence set forth in SEQ ID NO: 42 or 50, and a FR4 comprising a sequence set forth in SEQ ID NO: 43 or 51;
(iv) a VL comprising a FR1 comprising a sequence set forth in SEQ ID NO: 33, 34, 35 or 44, a FR2 comprising a sequence set forth between in SEQ ID NO: 36 or 45, a FR3 comprising a sequence set forth in SEQ ID NO: 37, 38 or 46, and a FR4 comprising a sequence set forth in SEQ ID NO: 39 or 47; or
(v) a VH comprising a FR1 comprising a sequence set forth in SEQ ID NO: 40 or 48, a FR2 comprising a sequence set forth between in SEQ ID NO: 41 or 49, a FR3 comprising a sequence set forth in SEQ ID NO: 42 or 50, and a FR4 comprising a sequence set forth in SEQ ID NO: 43 or 51; and a VL comprising a FR1 comprising a sequence set forth in SEQ ID NO: 33, 34, 35 or 44, a FR2 comprising a sequence set forth between in SEQ ID NO: 36 or 45, a FR3 comprising a sequence set forth in SEQ ID NO: 37, 38 or 46, and a FR4 comprising a sequence set forth in SEQ ID NO: 39 or 47.

P Embodiment 21

An antigen binding site according to any one of P embodiments 1 to 20, wherein the antigen binding site may be in the form of:
(i) a single chain Fv fragment (scFv);
(ii) a dimeric scFv (di-scFv);
(iii) one of (i) or (ii) linked to a constant region of an antibody, Fc or a heavy chain constant domain (CH) 2 and/or CH3; or
(iv) one of (i) or (ii) linked to a protein that binds to an immune effector cell.

P Embodiment 22

An antigen binding site according to any one of P embodiments 1 to 20, wherein the antigen binding site may be in the form of:
(i) a diabody;
(ii) a triabody;
(iii) a tetrabody;
(iv) a Fab;
(v) a F(ab')2;
(vi) a Fv;
(vii) one of (i) to (vi) linked to a constant region of an antibody, Fc or a heavy chain constant domain (CH) 2 and/or CH3; or
(viii) one of (i) to (vi) linked to a protein that binds to an immune effector cell.

P Embodiment 23

An antigen binding site according to any one of P embodiments 1 to 22, wherein the antigen binding site is in a non-conjugated form and is not adapted to form a conjugate.

P Embodiment 24

A fusion protein comprising an antigen binding site according to any one of P embodiments 1 to 23.

P Embodiment 25

A conjugate in the form of an antigen binding site or fusion protein according to any one of P embodiments 1 to 22, conjugated to a label or a cytotoxic agent.

P Embodiment 26

An antibody for binding to an antigen binding site, fusion protein, or conjugate according to any one of P embodiments 1 to 25.

P Embodiment 27

A nucleic acid encoding an antigen binding site, fusion protein or conjugate according to any one of P embodiments 1 to 26.

P Embodiment 28

A vector comprising the nucleic acid according to P embodiment 27.

P Embodiment 29

A cell comprising a vector or nucleic acid according to P embodiment 27 and 28.

P Embodiment 30

A pharmaceutical composition comprising an antigen binding site, fusion protein, or conjugate according to any one of P embodiments 1 to 26 and a pharmaceutically acceptable carrier, diluent or excipient.

P Embodiment 31

A kit or article of manufacture comprising an antigen binding site, fusion protein or conjugate according to any one of P embodiments 1 to 26.

P Embodiment 32

A method for treating or preventing an inflammatory disease or cancer in a subject, the method comprising administering an antigen binding site, fusion protein or conjugate according to any one of P embodiments 1 to 26.

P Embodiment 33

Use of an antigen binding site, fusion protein or conjugate according to any one of P embodiments 1 to 26 in the manufacture of a medicament for the treatment or prevention of an inflammatory disease or cancer.

P Embodiment 34

A C-X-C motif chemokine receptor 2 (CXCR2) antibody comprising a light chain variable region and a heavy chain variable region, wherein said light chain variable region comprises: a CDR L1 as set forth in SEQ ID NO:1, a CDR L2 as set forth in SEQ ID NO:2 and a CDR L3 as set forth in SEQ ID NO:3; and wherein said heavy chain variable region comprises: a CDR H1 as set forth in SEQ ID NO:4, a CDR H2 as set forth in SEQ ID NO:5, and a CDR H3 as set forth in SEQ ID NO:6.

P Embodiment 35

A C-X-C motif chemokine receptor 2 (CXCR2) antibody comprising a light chain variable region and a heavy chain variable region, wherein said light chain variable region comprises: a CDR L1 as set forth in SEQ ID NO:11, a CDR L2 as set forth in SEQ ID NO:12 and a CDR L3 as set forth in SEQ ID NO:13; and wherein said heavy chain variable region comprises: a CDR H1 as set forth in SEQ ID NO:14, a CDR H2 as set forth in SEQ ID NO:15, and a CDR H3 as set forth in SEQ ID NO:16.

P Embodiment 36

A C-X-C motif chemokine receptor 2 (CXCR2) antibody comprising a light chain variable region and a heavy chain variable region, wherein said light chain variable region comprises: a CDR L1 as set forth in SEQ ID NO:21, a CDR L2 as set forth in SEQ ID NO:22 and a CDR L3 as set forth in SEQ ID NO:23; and wherein said heavy chain variable region comprises: a CDR H1 as set forth in SEQ ID NO:24, a CDR H2 as set forth in SEQ ID NO:25, and a CDR H3 as set forth in SEQ ID NO:26.

P Embodiment 37

The CXCR2 antibody of one of P embodiments 34 to 36, wherein said antibody is a humanized antibody.

P Embodiment 38

The CXCR2 antibody of one of P embodiments 34 to 36, wherein said antibody is a chimeric antibody.

P Embodiment 39

The CXCR2 antibody of one of P embodiments 34 to 36, wherein said antibody is a Fab' fragment.

P Embodiment 40

The CXCR2 antibody of one of P embodiments 34 to 36, wherein said antibody is a single chain antibody (scFv).

P Embodiment 41

The CXCR2 antibody of one of P embodiments 34 to 36, wherein said light chain variable region comprises: a Val or Asp at a position corresponding to Kabat position 1; an Ile, Val or Ala at a position corresponding to Kabat position 2; a Thr, Ala or Ser at a position corresponding to Kabat position 7; a Ser or Thr at a position corresponding to Kabat position 14;
a Leu or Pro at a position corresponding to Kabat position 15; an Asp or Glu at a position corresponding to Kabat position 17; a Gln or Pro at a position corresponding to Kabat position 18; a Lys or Gln at a position corresponding to Kabat position 45; a Ser or Ala at a position corresponding to Kabat position 67; a Leu or Val at a position corresponding to Kabat position 83; and/or a Gly or Gln at a position corresponding to Kabat position 100.

P Embodiment 42

The CXCR2 antibody of one of P embodiments 34 to 36 or 41, wherein said heavy chain variable region comprises: a Gln or Val at a position corresponding to Kabat position 5; a Pro or Ala at a position corresponding to Kabat position 9; a Leu or Val at a position corresponding to Kabat position 11; a Val or Lys at a position corresponding to Kabat position 12; an Ile or Val at a position corresponding to Kabat position 20; a Lys or Arg at a position corresponding to Kabat position 38; an Arg or Ala at a position corresponding to Kabat position 40; a Lys or Gln at a position corresponding to Kabat position 43; a Lys or Arg at a position corresponding to Kabat position 44; a Ser or Ala at a position corresponding to Kabat position 75; a Gln or Glu at a position corresponding to Kabat position 81; a Thr or Arg at a position corresponding to Kabat position 83; and/or a Ser or Thr at a position corresponding to Kabat position 87.

P Embodiment 43

The CXCR2 antibody of one of P embodiments 34 to 36, wherein said light chain variable region comprises the sequence of SEQ ID NO:7, SEQ ID NO:17, SEQ ID NO:27 or NO:31.

P Embodiment 44

The CXCR2 antibody of one of P embodiments 34 to 36, wherein said heavy chain variable region comprises the sequence of SEQ ID NO:8, SEQ ID NO:18, SEQ ID NO:28 or NO:32.

P Embodiment 45

The CXCR2 antibody of one of P embodiments 34 to 36, wherein said light chain variable region comprises a FR L1 as set forth in SEQ ID NO:33, FR L2 as set forth in SEQ ID NO:36, a FR L3 as set forth in SEQ ID NO:37 and a FR L4 as set forth in SEQ ID NO:39.

P Embodiment 46

The CXCR2 antibody of one of P embodiments 34 to 36, wherein said light chain variable region comprises a FR L1 as set forth in SEQ ID NO:34, FR L2 as set forth in SEQ ID NO:36, a FR L3 as set forth in SEQ ID NO:37 and a FR L4 as set forth in SEQ ID NO:39.

P Embodiment 47

The CXCR2 antibody of one of P embodiments 34 to 36, wherein said light chain variable region comprises a FR L1 as set forth in SEQ ID NO:35, FR L2 as set forth in SEQ ID NO:36, a FR L3 as set forth in SEQ ID NO:38 and a FR L4 as set forth in SEQ ID NO:39.

P Embodiment 48

The CXCR2 antibody of one of P embodiments 34 to 36, wherein said light chain variable region comprises a FR L1 as set forth in SEQ ID NO:44, FR L2 as set forth in SEQ ID NO:45, a FR L3 as set forth in SEQ ID NO:46 and a FR L4 as set forth in SEQ ID NO:47.

P Embodiment 49

The CXCR2 antibody of one of P embodiments 34 to 36, wherein said heavy chain variable region comprises a FR H1 as set forth in SEQ ID NO:40, FR H2 as set forth in SEQ ID NO:41, a FR H3 as set forth in SEQ ID NO:42 and a FR H4 as set forth in SEQ ID NO:43.

P Embodiment 50

The CXCR2 antibody of one of P embodiments 34 to 36, wherein said heavy chain variable region comprises a FR H1 as set forth in SEQ ID NO:48, FR H2 as set forth in SEQ ID NO:49, a FR H3 as set forth in SEQ ID NO:50 and a FR H4 as set forth in SEQ ID NO:51.

P Embodiment 51

The CXCR2 antibody of one of P embodiments 34 to 48, wherein said antibody is an IgG.

P Embodiment 52

The CXCR2 antibody of one of P embodiments 34 to 49, wherein said antibody is an IgG4.

P Embodiment 53

An isolated nucleic acid encoding a CXCR2 antibody of one of P embodiments 34 to 50.

P Embodiment 54

A pharmaceutical composition comprising a therapeutically effective amount of a CXCR2 antibody of one of P embodiments 34 to 50 and a pharmaceutically acceptable excipient.

P Embodiment 55

A cell comprising a CXCR2 antibody of one of P embodiments 34 to 50.

P Embodiment 56

A method of treating an inflammatory disease or cancer in a subject in need thereof, said method comprising administering to a subject a therapeutically effective amount of a CXCR2 antibody of one of P embodiments 34 to 50, thereby treating said inflammatory disease or cancer in said subject.

EMBODIMENTS

Embodiment 1

A C-X-C motif chemokine receptor 2 (CXCR2) antibody comprising a light chain variable region and a heavy chain variable region,
wherein said light chain variable region comprises:
a CDR L1 as set forth in SEQ ID NO:1, a CDR L2 as set forth in SEQ ID NO:2 and a CDR L3 as set forth in SEQ ID NO:3; and wherein said heavy chain variable region comprises:
a CDR H1 as set forth in SEQ ID NO:4, a CDR H2 as set forth in SEQ ID NO:5, and a CDR H3 as set forth in SEQ ID NO:6.

Embodiment 2

A C-X-C motif chemokine receptor 2 (CXCR2) antibody comprising a light chain variable region and a heavy chain variable region,
wherein said light chain variable region comprises:
a CDR L1 as set forth in SEQ ID NO:11, a CDR L2 as set forth in SEQ ID NO:12 and a CDR L3 as set forth in SEQ ID NO:13; and
wherein said heavy chain variable region comprises:
a CDR H1 as set forth in SEQ ID NO:14, a CDR H2 as set forth in SEQ ID NO:15, and a CDR H3 as set forth in SEQ ID NO:16.

Embodiment 3

A C-X-C motif chemokine receptor 2 (CXCR2) antibody comprising a light chain variable region and a heavy chain variable region,
wherein said light chain variable region comprises:
a CDR L1 as set forth in SEQ ID NO:21, a CDR L2 as set forth in SEQ ID NO:22 and a CDR L3 as set forth in SEQ ID NO:23; and
wherein said heavy chain variable region comprises:
a CDR H1 as set forth in SEQ ID NO:24, a CDR H2 as set forth in SEQ ID NO:25, and a CDR H3 as set forth in SEQ ID NO:26.

Embodiment 4

A C-X-C motif chemokine receptor 2 (CXCR2) antibody comprising a light chain variable region and a heavy chain variable region,
wherein said light chain variable region comprises:
a CDR L1 as set forth in SEQ ID NO:1, a CDR L2 as set forth in SEQ ID NO:2 and a CDR L3 as set forth in SEQ ID NO:3; and
wherein said heavy chain variable region comprises:
a CDR H1 as set forth in SEQ ID NO:58, a CDR H2 as set forth in SEQ ID NO:5, and a CDR H3 as set forth in SEQ ID NO:6.

Embodiment 5

The CXCR2 antibody of one of embodiments 1 to 4, wherein said antibody is a humanized antibody.

Embodiment 6

The CXCR2 antibody of one of embodiments 1 to 4, wherein said antibody is a chimeric antibody.

Embodiment 7

The CXCR2 antibody of one of embodiments 1 to 4, wherein said antibody is a Fab' fragment.

Embodiment 8

The CXCR2 antibody of one of embodiments 1 to 4, wherein said antibody is a single chain antibody (scFv).

Embodiment 9

The CXCR2 antibody of one of embodiments 1 to 4, wherein said light chain variable region comprises:
a Val or Asp at a position corresponding to Kabat position 1;
an Ile, Val or Ala at a position corresponding to Kabat position 2;
a Thr, Ala or Ser at a position corresponding to Kabat position 7;
a Ser or Thr at a position corresponding to Kabat position 14;
a Leu or Pro at a position corresponding to Kabat position 15;
an Asp or Glu at a position corresponding to Kabat position 17;
a Gln or Pro at a position corresponding to Kabat position 18;
a Lys or Gln at a position corresponding to Kabat position 45;
a Glu or Gln at a position corresponding to Kabat position 47;
a Ser or Ala at a position corresponding to Kabat position 67;
a Leu or Val at a position corresponding to Kabat position 83; and/or
a Gly or Gln at a position corresponding to Kabat position 100.

Embodiment 10

The CXCR2 antibody of one of embodiments 1 to 4 or 99, wherein said heavy chain variable region comprises:
a Gln or Val at a position corresponding to Kabat position 5;
a Pro or Ala at a position corresponding to Kabat position 9;
a Leu or Val at a position corresponding to Kabat position 11;
a Val or Lys at a position corresponding to Kabat position 12;
an Ile or Val at a position corresponding to Kabat position 20;
a Lys or Arg at a position corresponding to Kabat position 38;
an Arg or Ala at a position corresponding to Kabat position 40;
a Lys or Gln at a position corresponding to Kabat position 43;
a Lys or Arg at a position corresponding to Kabat position 44;
a Ser or Ala at a position corresponding to Kabat position 75;
a Gln or Glu at a position corresponding to Kabat position 81;
a Thr or Arg at a position corresponding to Kabat position 83; and/or
a Ser or Thr at a position corresponding to Kabat position 87

Embodiment 11

The CXCR2 antibody of one of embodiments 1 to 4, wherein said light chain variable region comprises the sequence of SEQ ID NO:7, SEQ ID NO:17, SEQ ID NO:27, SEQ ID NO:31 and SEQ ID NO:57.

Embodiment 12

The CXCR2 antibody of one of embodiments 1 to 4, wherein said heavy chain variable region comprises the sequence of SEQ ID NO:8, SEQ ID NO:18, SEQ ID NO:28, SEQ ID NO:32 or SEQ ID NO:56.

Embodiment 13

The CXCR2 antibody of one of embodiments 1 to 4, wherein said light chain variable region comprises a FR L1 as set forth in SEQ ID NO:33, FR L2 as set forth in SEQ ID NO:36, a FR L3 as set forth in SEQ ID NO:37 and a FR L4 as set forth in SEQ ID NO:39.

Embodiment 14

The CXCR2 antibody of one of embodiments 1 to 4, wherein said light chain variable region comprises a FR L1 as set forth in SEQ ID NO:44, FR L2 as set forth in SEQ ID NO:59, a FR L3 as set forth in SEQ ID NO:46 and a FR L4 as set forth in SEQ ID NO:47.

Embodiment 15

The CXCR2 antibody of one of embodiments 1 to 4, wherein said light chain variable region comprises a FR L1 as set forth in SEQ ID NO:34, FR L2 as set forth in SEQ ID NO:36, a FR L3 as set forth in SEQ ID NO:37 and a FR L4 as set forth in SEQ ID NO:39.

Embodiment 16

The CXCR2 antibody of one of embodiments 1 to 4, wherein said light chain variable region comprises a FR L1 as set forth in SEQ ID NO:35, FR L2 as set forth in SEQ ID NO:36, a FR L3 as set forth in SEQ ID NO:38 and a FR L4 as set forth in SEQ ID NO:39.

Embodiment 17

The CXCR2 antibody of one of embodiments 1 to 4, wherein said light chain variable region comprises a FR L1 as set forth in SEQ ID NO:44, FR L2 as set forth in SEQ ID NO:45, a FR L3 as set forth in SEQ ID NO:46 and a FR L4 as set forth in SEQ ID NO:47.

Embodiment 18

The CXCR2 antibody of one of embodiments 1 to 4, wherein said heavy chain variable region comprises a FR H1 as set forth in SEQ ID NO:40, FR H2 as set forth in SEQ ID NO:41, a FR H3 as set forth in SEQ ID NO:42 and a FR H4 as set forth in SEQ ID NO:43.

Embodiment 19

The CXCR2 antibody of one of embodiments 1 to 4, wherein said heavy chain variable region comprises a FR H1 as set forth in SEQ ID NO:48, FR H2 as set forth in SEQ ID NO:49, a FR H3 as set forth in SEQ ID NO:50 and a FR H4 as set forth in SEQ ID NO:51.

Embodiment 20

The CXCR2 antibody of one of embodiments 1 to 19, wherein said antibody is an IgG.

Embodiment 21

The CXCR2 antibody of one of embodiments 1 to 20, wherein said antibody is an IgG4.

Embodiment 22

An isolated nucleic acid encoding a CXCR2 antibody of one of embodiments 1 to 21.

Embodiment 23

A pharmaceutical composition comprising a therapeutically effective amount of a CXCR2 antibody of one of embodiments 1 to 21 and a pharmaceutically acceptable excipient.

Embodiment 24

A cell comprising a CXCR2 antibody of one of embodiments 1 to 21.

Embodiment 25

A method of treating an inflammatory disease or cancer in a subject in need thereof, said method comprising administering to a subject a therapeutically effective amount of a CXCR2 antibody of one of embodiments 1 to 21, thereby treating said inflammatory disease or cancer in said subject.

What is claimed is:

1. A C-X-C motif chemokine receptor 2 (CXCR2) antibody comprising a light chain variable region and a heavy chain variable region, wherein said light chain variable region comprises:
   a CDR L1 as set forth in SEQ ID NO:1, a CDR L2 as set forth in SEQ ID NO:2 and a CDR L3 as set forth in SEQ ID NO:3; and
   wherein said heavy chain variable region comprises:
   a CDR H1 as set forth in SEQ ID NO:4, a CDR H2 as set forth in SEQ ID NO:5, and a CDR H3 as set forth in SEQ ID NO:6.

2. The CXCR2 antibody of claim 1, wherein said light chain variable region comprises:
   a Val or Asp at a position corresponding to Kabat position 1 of the sequence of SEQ ID NO:31;
   an Ile, Val or Ala at a position corresponding to Kabat position 2 of the sequence of SEQ ID NO:31;
   a Thr, Ala or Ser at a position corresponding to Kabat position 7 of the sequence of SEQ ID NO:31;
   a Ser or Thr at a position corresponding to Kabat position 14 of the sequence of SEQ ID NO:31;
   a Leu or Pro at a position corresponding to Kabat position 15 of the sequence of SEQ ID NO:31;
   an Asp or Glu at a position corresponding to Kabat position 17 of the sequence of SEQ ID NO:31;
   a Gln or Pro at a position corresponding to Kabat position 18 of the sequence of SEQ ID NO:31;
   a Lys or Gln at a position corresponding to Kabat position 45 of the sequence of SEQ ID NO:31;
   a Glu or Gln at a position corresponding to Kabat position 47 of the sequence of SEQ ID NO:31;
   a Ser or Ala at a position corresponding to Kabat position 67 of the sequence of SEQ ID NO:31;
   a Leu or Val at a position corresponding to Kabat position 83 of the sequence of SEQ ID NO:31; or
   a Gly or Gln at a position corresponding to Kabat position 100 of the sequence of SEQ ID NO:31.

3. The CXCR2 antibody of claim 1, wherein said heavy chain variable region comprises:
   a Gln or Val at a position corresponding to Kabat position 5 of the sequence of SEQ ID NO:32;
   a Pro or Ala at a position corresponding to Kabat position 9 of the sequence of SEQ ID NO:32;
   a Leu or Val at a position corresponding to Kabat position 11 of the sequence of SEQ ID NO:32;
   a Val or Lys at a position corresponding to Kabat position 12 of the sequence of SEQ ID NO:32;
   an Ile or Val at a position corresponding to Kabat position 20 of the sequence of SEQ ID NO:32;
   a Lys or Arg at a position corresponding to Kabat position 38 of the sequence of SEQ ID NO:32;
   an Arg or Ala at a position corresponding to Kabat position 40 of the sequence of SEQ ID NO:32;
   a Lys or Gln at a position corresponding to Kabat position 43 of the sequence of SEQ ID NO:32;
   a Lys or Arg at a position corresponding to Kabat position 44 of the sequence of SEQ ID NO:32;
   a Ser or Ala at a position corresponding to Kabat position 75 of the sequence of SEQ ID NO:32;
   a Gln or Glu at a position corresponding to Kabat position 81 of the sequence of SEQ ID NO:32;
   a Thr or Arg at a position corresponding to Kabat position 83 of the sequence of SEQ ID NO:32; or
   a Ser or Thr at a position corresponding to Kabat position 87 of the sequence of SEQ ID NO:32.

4. A pharmaceutical composition comprising a therapeutically effective amount of a CXCR2 antibody of claim 1 and a pharmaceutically acceptable excipient.

* * * * *

SEQUENCE LISTING

```
<160> NUMBER OF SEQ ID NOS: 62

<210> SEQ ID NO 1
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 1

Gln Ser Leu Val His Ser Asn Gly Asn Thr Tyr
1               5                   10

<210> SEQ ID NO 2
<211> LENGTH: 3
<212> TYPE: PRT
<213> ORGANISM: Artificial sequence
<220> FEATURE:
```

```
<223> OTHER INFORMATION: Synthetic Polypeptide

<400> SEQUENCE: 2

Lys Val Ser
1

<210> SEQ ID NO 3
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 3

Ser Gln Gly Thr His Val Pro Tyr Thr
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 4

Gly Tyr Ala Phe Ser Asn Ser Trp
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 5

Ile Tyr Pro Gly Asp Gly Asn Ile
1               5

<210> SEQ ID NO 6
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 6

Ala Arg Ser Phe Leu Tyr Val Asp Phe Asp Tyr
1               5                   10

<210> SEQ ID NO 7
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 7

Val Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
            100                 105                 110

Arg

<210> SEQ ID NO 8
<211> LENGTH: 118
<212> TYPE: PRT
<213> ORGANISM: Artificial sequence
<220> FEATURE:
<223> OTHER INFORMATION: Synthetic Polypeptide

<400> SEQUENCE: 8

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asn Ser
                20                  25                  30

Trp Met Asn Trp Val Lys Gln Arg Pro Gly Lys Gly Leu Glu Trp Ile
            35                  40                  45

Gly Arg Ile Tyr Pro Gly Asp Gly Asn Ile Asn Tyr Tyr Gly Lys Phe
        50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Ser Phe Leu Tyr Val Asp Phe Asp Tyr Trp Gly Gln Gly Thr
            100                 105                 110

Thr Leu Thr Val Ser Ser
        115

<210> SEQ ID NO 9
<211> LENGTH: 339
<212> TYPE: DNA
<213> ORGANISM: Artificial sequence
<220> FEATURE:
<223> OTHER INFORMATION: Synthetic Polynucleotide

<400> SEQUENCE: 9
gttattgtga tgacccaaac tccactctcc ctgcctgtca gtcttggaga tcaagcctcc      60
atctcttgca gatctagtca gagccttgta cacagtaatg gaaacaccta tttacaatgg    120
tatctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaggtac acatgttccg    300
tacacgttcg gaggggggac caagctggaa ataaaacgg                           339

<210> SEQ ID NO 10
<211> LENGTH: 354
<212> TYPE: DNA
<213> ORGANISM: Artificial sequence
<220> FEATURE:
<223> OTHER INFORMATION: Synthetic Polynucleotide

<400> SEQUENCE: 10

```
caggttcagc tgcagcagtc tggacctgag ctggtgaagc ctggggcctc agtgaagatt      60
tcctgcaagg cttctggcta cgcattcagt aactcctgga tgaactgggt gaagcagagg    120
cctggaaagg gtcttgagtg gattggacgg atttatcctg agatggaaa tattaactac     180 tatgggaagt tcaaggacaa ggccacactg actgcagaca atcctccaa cacagcctac     240 atgcaactca gcagcctgac atctgaggac tctgcggtct acttctgtgc aaggagtttt   300
ctctacgtgg actttgacta ctggggccaa ggcaccactc tcacagtctc ctca          354
```

<210> SEQ ID NO 11
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 11

Gln Thr Leu Val His Ser Asn Gly Asn Thr Tyr
1               5                   10

<210> SEQ ID NO 12
<211> LENGTH: 3
<212> TYPE: PRT
<213> ORGANISM: Artificial sequence
<220> FEATURE:
<223> OTHER INFORMATION: Synthetic Polypeptide

<400> SEQUENCE: 12

Lys Val Ser
1

<210> SEQ ID NO 13
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 13

Ser Gln Gly Thr His Val Pro Tyr Thr
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 14

Gly Tyr Ala Phe Ser Asn Ser Trp
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 15

Ile Tyr Pro Gly Asp Gly Asn Ile
1               5

<210> SEQ ID NO 16

<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 16

Ala Arg Ser Phe Leu Tyr Val Asp Phe Asp Tyr
1               5                   10

<210> SEQ ID NO 17
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 17

Asp Val Val Met Thr Gln Ala Pro Leu Ser Leu Pro Val Ser Leu Gly
1               5                   10                  15

Asp Gln Ala Ser Ile Ser Cys Arg Ser Ser Gln Thr Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Tyr Thr Phe Gly Gly Gly Thr Lys Leu Glu Ile Lys
            100                 105                 110

Arg

<210> SEQ ID NO 18
<211> LENGTH: 118
<212> TYPE: PRT
<213> ORGANISM: Artificial sequence
<220> FEATURE:
<223> OTHER INFORMATION: Synthetic Polypeptide

<400> SEQUENCE: 18

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asn Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asn Ile Asn Tyr Gly Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Ser Phe Leu Tyr Val Asp Phe Asp Tyr Trp Gly Gln Gly Thr
            100                 105                 110

Thr Leu Thr Val Ser Ser
        115

```
<210> SEQ ID NO 19
<211> LENGTH: 339
<212> TYPE: DNA
<213> ORGANISM: Artificial sequence
<220> FEATURE:
<223> OTHER INFORMATION: Synthetic Polynucleotide

<400> SEQUENCE: 19
gatgttgtga tgacccaagc tccactctcc ctgcctgtca gtcttggaga tcaagcctcc      60
atctcttgca ggtctagtca gacccttgta cacagtaatg aaacaccta tttacaatgg     120 tatctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaggtac acatgttccg    300
tacacgttcg gagggggac caagctggaa ataaaacgg                            339

<210> SEQ ID NO 20
<211> LENGTH: 354
<212> TYPE: DNA
<213> ORGANISM: Artificial sequence
<220> FEATURE:
<223> OTHER INFORMATION: Synthetic Polynucleotide

<400> SEQUENCE: 20
caggttcagc tgcagcagtc tggacctgag ctggtgaagc ctggggcctc agtgaagatt     60
tcctgcaagg cttctggcta cgcattcagt aactcctgga tgaactgggt gaagcagagg    120
cctggaaagg gtcttgagtg gattggacgg atttatcctg agatggaaa tattaactac    180 tatgggaagt tcaaggacaa ggccacactg actgcagaca atcctccaa cacagcctac    240 atgcaactca gcagcctgac atctgaggac tctgcggtct acttctgtgc aaggagtttt    300
ctctacgtgg actttgacta ctgggggccaa ggcaccactc tcacagtctc ctca         354

<210> SEQ ID NO 21
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 21

Gln Ser Leu Val His Ser Asn Gly Asn Thr Tyr
 1               5                  10

<210> SEQ ID NO 22
<211> LENGTH: 3
<212> TYPE: PRT
<213> ORGANISM: Artificial sequence
<220> FEATURE:
<223> OTHER INFORMATION: Synthetic Polypeptide

<400> SEQUENCE: 22

Lys Leu Ser
 1

<210> SEQ ID NO 23
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 23
```

```
Ser Gln Ser Thr His Val Pro Tyr Thr
1               5

<210> SEQ ID NO 24
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 24

Gly Tyr Ala Phe Ser Asn Ser Trp
1               5

<210> SEQ ID NO 25
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 25

Ile Tyr Pro Gly Asp Gly Asn Ile
1               5

<210> SEQ ID NO 26
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 26

Ala Arg Ser Phe Leu Tyr Val Tyr Phe Asp Tyr
1               5                   10

<210> SEQ ID NO 27
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 27

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
                100                 105                 110

Arg

<210> SEQ ID NO 28
<211> LENGTH: 118
<212> TYPE: PRT
```

<213> ORGANISM: Artificial sequence
<220> FEATURE:
<223> OTHER INFORMATION: Synthetic Polypeptide

<400> SEQUENCE: 28

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asn Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asn Ile Asn Tyr Tyr Gly Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Ser Phe Leu Tyr Val Tyr Phe Asp Tyr Trp Gly Gln Gly Thr
            100                 105                 110

Thr Leu Thr Val Ser Ser
        115
```

<210> SEQ ID NO 29
<211> LENGTH: 339
<212> TYPE: DNA
<213> ORGANISM: Artificial sequence
<220> FEATURE:
<223> OTHER INFORMATION: Synthetic Polynucleotide

<400> SEQUENCE: 29

| gatgctgtga tgacccaaac tccactctcc ctgcctgtca gtcttggaga tcaagcctcc | 60 |
| atctcttgca gatctagtca gagccttgta cacagtaatg gaaacaccta tttacaatgg | 120 |
| tatctgcaga agccaggcca gtctccaaag ctcctgatct acaaactttc caaccgattt | 180 |
| tctgggtcc cagacaggtt cagtggcagt ggagcaggga cagatttcac actcaagatc | 240 |
| agcagagtgg aggctgagga tctgggagtt tatttctgct ctcaaagtac acatgttccg | 300 |
| tacacgttcg agggggggac caagctggaa ataaaacgg | 339 |

<210> SEQ ID NO 30
<211> LENGTH: 354
<212> TYPE: DNA
<213> ORGANISM: Artificial sequence
<220> FEATURE:
<223> OTHER INFORMATION: Synthetic Polynucleotide

<400> SEQUENCE: 30

| caggttcagc tgcagcagtc tggacctgaa ctggtgaagc ctggggcctc agtgaagatt | 60 |
| tcctgtaagg cttctggcta cgcattcagt aactcctgga tgaactgggt gaagcagagg | 120 |
| cctggaaagg gtcttgagtg gattggacgg atttatcctg gagatggaaa tattaactac | 180 |
| tatgggaagt tcaaggacaa ggccacactg actgcagaca atcctccaa cacagcctac | 240 |
| atgcaactca gcagcctgac atctgaggac tctgcggtct acttctgtgc aaggagtttt | 300 |
| ctctacgtgt actttgacta ctggggccaa ggcaccactc tcacagtctc ctca | 354 |

<210> SEQ ID NO 31
<211> LENGTH: 113
<212> TYPE: PRT
<213> ORGANISM: Artificial sequence

```
<220> FEATURE:
<223> OTHER INFORMATION: Synthetic Polypeptide

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Gly
                85                  90                  95

Thr His Val Pro Tyr Thr Phe Gly Gln Gly Thr Lys Leu Glu Ile Lys
            100                 105                 110

Arg

<210> SEQ ID NO 32
<211> LENGTH: 118
<212> TYPE: PRT
<213> ORGANISM: Artificial sequence
<220> FEATURE:
<223> OTHER INFORMATION: Synthetic Polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asn Ile Asn Tyr Tyr Lys Phe
    50                  55                  60

Lys Asp Lys Ala Thr Leu Thr Ala Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Ala Arg Ser Phe Leu Tyr Val Asp Phe Asp Tyr Trp Gly Gln Gly Thr
            100                 105                 110

Thr Leu Thr Val Ser Ser
        115

<210> SEQ ID NO 33
<211> LENGTH: 26
<212> TYPE: PRT
<213> ORGANISM: Artificial sequence
<220> FEATURE:
<223> OTHER INFORMATION: Synthetic Polypeptide

<400> SEQUENCE: 33

Val Ile Val Met Thr Gln Thr Pro Leu Ser Leu Pro Val Ser Leu Gly
1               5                   10                  15

Asp Gln Ala Ser Ile Ser Cys Arg Ser Ser
            20                  25
```

```
<210> SEQ ID NO 34
<211> LENGTH: 26
<212> TYPE: PRT
<213> ORGANISM: Artificial sequence
<220> FEATURE:
<223> OTHER INFORMATION: Synthetic Polypeptide

<400> SEQUENCE: 34

Asp Val Val Met Thr Gln Ala Pro Leu Ser Leu Pro Val Ser Leu Gly
1               5                   10                  15

Asp Gln Ala Ser Ile Ser Cys Arg Ser Ser
            20                  25

<210> SEQ ID NO 35
<211> LENGTH: 26
<212> TYPE: PRT
<213> ORGANISM: Artificial sequence
<220> FEATURE:
<223> OTHER INFORMATION: Synthetic Polypeptide

<400> SEQUENCE: 35

Asp Ala Val Met Thr Gln Thr Pro Leu Ser Leu Pro Val Ser Leu Gly
1               5                   10                  15

Asp Gln Ala Ser Ile Ser Cys Arg Ser Ser
            20                  25

<210> SEQ ID NO 36
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 36

Leu Gln Trp Tyr Leu Gln Lys Pro Gly Gln Ser Pro Lys Leu Leu Ile
1               5                   10                  15

Tyr

<210> SEQ ID NO 37
<211> LENGTH: 36
<212> TYPE: PRT
<213> ORGANISM: Artificial sequence
<220> FEATURE:
<223> OTHER INFORMATION: Synthetic Polypeptide

<400> SEQUENCE: 37

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 38
<211> LENGTH: 36
<212> TYPE: PRT
<213> ORGANISM: Artificial sequence
<220> FEATURE:
<223> OTHER INFORMATION: Synthetic Polypeptide

<400> SEQUENCE: 38

Asn Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Leu Gly
```

```
                    20                  25                  30

Val Tyr Phe Cys
        35

<210> SEQ ID NO 39
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 39

Phe Gly Gly Gly Thr Lys Leu Glu Ile Lys Arg
1               5                   10

<210> SEQ ID NO 40
<211> LENGTH: 25
<212> TYPE: PRT
<213> ORGANISM: Artificial sequence
<220> FEATURE:
<223> OTHER INFORMATION: Synthetic Polypeptide

<400> SEQUENCE: 40

Gln Val Gln Leu Gln Gln Ser Gly Pro Glu Leu Val Lys Pro Gly Ala
1               5                   10                  15

Ser Val Lys Ile Ser Cys Lys Ala Ser
            20                  25

<210> SEQ ID NO 41
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 41

Met Asn Trp Val Lys Gln Arg Pro Gly Lys Gly Leu Glu Trp Ile Gly
1               5                   10                  15

Arg

<210> SEQ ID NO 42
<211> LENGTH: 38
<212> TYPE: PRT
<213> ORGANISM: Artificial sequence
<220> FEATURE:
<223> OTHER INFORMATION: Synthetic Polypeptide

<400> SEQUENCE: 42

Asn Tyr Tyr Gly Lys Phe Lys Asp Lys Ala Thr Leu Thr Ala Asp Lys
1               5                   10                  15

Ser Ser Asn Thr Ala Tyr Met Gln Leu Ser Ser Leu Thr Ser Glu Asp
            20                  25                  30

Ser Ala Val Tyr Phe Cys
        35

<210> SEQ ID NO 43
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 43

Trp Gly Gln Gly Thr Thr Leu Thr Val Ser Ser
```

```
<210> SEQ ID NO 44
<211> LENGTH: 26
<212> TYPE: PRT
<213> ORGANISM: Artificial sequence
<220> FEATURE:
<223> OTHER INFORMATION: Synthetic Polypeptide

<400> SEQUENCE: 44

Asp Ile Val Met Thr Gln Ser Pro Leu Ser Leu Pro Val Thr Pro Gly
 1               5                  10                  15

Glu Pro Ala Ser Ile Ser Cys Arg Ser Ser
            20                  25

<210> SEQ ID NO 45
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 45

Leu Gln Trp Tyr Leu Gln Lys Pro Gly Gln Ser Pro Gln Leu Leu Ile
 1               5                  10                  15

Tyr

<210> SEQ ID NO 46
<211> LENGTH: 36
<212> TYPE: PRT
<213> ORGANISM: Artificial sequence
<220> FEATURE:
<223> OTHER INFORMATION: Synthetic Polypeptide

<400> SEQUENCE: 46

Asn Arg Phe Ser Gly Val Pro Asp Arg Phe Ser Gly Ser Gly Ser Gly
 1               5                  10                  15

Thr Asp Phe Thr Leu Lys Ile Ser Arg Val Glu Ala Glu Asp Val Gly
            20                  25                  30

Val Tyr Phe Cys
        35

<210> SEQ ID NO 47
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 47

Phe Gly Gln Gly Thr Lys Leu Glu Ile Lys Arg
 1               5                  10

<210> SEQ ID NO 48
<211> LENGTH: 25
<212> TYPE: PRT
<213> ORGANISM: Artificial sequence
<220> FEATURE:
<223> OTHER INFORMATION: Synthetic Polypeptide

<400> SEQUENCE: 48

Gln Val Gln Leu Val Gln Ser Gly Ala Glu Val Lys Lys Pro Gly Ala
 1               5                  10                  15

Ser Val Lys Val Ser Cys Lys Ala Ser
```

<210> SEQ ID NO 49
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 49

Met Asn Trp Val Arg Gln Ala Pro Gly Gln Arg Leu Glu Trp Ile Gly
1               5                   10                  15

Arg

<210> SEQ ID NO 50
<211> LENGTH: 38
<212> TYPE: PRT
<213> ORGANISM: Artificial sequence
<220> FEATURE:
<223> OTHER INFORMATION: Synthetic Polypeptide

<400> SEQUENCE: 50

Asn Tyr Tyr Gly Lys Phe Lys Asp Lys Ala Thr Leu Thr Ala Asp Lys
1               5                   10                  15

Ser Ala Asn Thr Ala Tyr Met Glu Leu Ser Ser Leu Arg Ser Glu Asp
            20                  25                  30

Thr Ala Val Tyr Phe Cys
        35

<210> SEQ ID NO 51
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 51

Trp Gly Gln Gly Thr Thr Leu Thr Val Ser Ser
1               5                   10

<210> SEQ ID NO 52
<211> LENGTH: 360
<212> TYPE: PRT
<213> ORGANISM: Artificial sequence
<220> FEATURE:
<223> OTHER INFORMATION: Synthetic Polypeptide

<400> SEQUENCE: 52

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

```
Ile Phe Gly Thr Phe Leu Cys Lys Val Val Ser Leu Leu Lys Glu Val
            115                 120                 125

Asn Phe Tyr Ser Gly Ile Leu Leu Ala Cys Ile Ser Val Asp Arg
        130                 135                 140

Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu
                165                 170                 175

Ala Leu Pro Val Leu Leu Phe Arg Arg Thr Val Tyr Ser Ser Asn Val
            180                 185                 190

Ser Pro Ala Cys Tyr Glu Asp Met Gly Asn Asn Thr Ala Asn Trp Arg
        195                 200                 205

Met Leu Leu Arg Ile Leu Pro Gln Ser Phe Gly Phe Ile Val Pro Leu
    210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
            260                 265                 270

Ala Asp Thr Leu Met Arg Thr Gln Val Ile Gln Glu Thr Cys Glu Arg
        275                 280                 285

Arg Asn His Ile Asp Arg Ala Leu Asp Ala Thr Glu Ile Leu Gly Ile
    290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
            340                 345                 350

Ser Gly His Thr Ser Thr Thr Leu
        355                 360

<210> SEQ ID NO 53
<211> LENGTH: 21
<212> TYPE: PRT
<213> ORGANISM: Artificial sequence
<220> FEATURE:
<223> OTHER INFORMATION: Synthetic Polypeptide

<400> SEQUENCE: 53

Met Glu Asp Phe Asn Met Glu Ser Asp Ser Phe Glu Asp Phe Trp Lys
1               5                   10                  15

Gly Glu Asp Leu Ser
            20

<210> SEQ ID NO 54
<211> LENGTH: 29
<212> TYPE: PRT
<213> ORGANISM: Artificial sequence
<220> FEATURE:
<223> OTHER INFORMATION: Synthetic Polypeptide

<400> SEQUENCE: 54

Leu Ser Asn Tyr Ser Tyr Ser Ser Thr Leu Pro Pro Phe Leu Leu Asp
1               5                   10                  15

Ala Ala Pro Cys Glu Pro Glu Ser Leu Glu Ile Asn Lys
```

```
<210> SEQ ID NO 55
<211> LENGTH: 22
<212> TYPE: PRT
<213> ORGANISM: Artificial sequence
<220> FEATURE:
<223> OTHER INFORMATION: Synthetic Polypeptide

<400> SEQUENCE: 55

Ser Phe Glu Asp Phe Trp Lys Gly Glu Asp Leu Ser Asn Tyr Ser Tyr
1               5                   10                  15

Ser Ser Thr Leu Pro Pro
            20

<210> SEQ ID NO 56
<211> LENGTH: 117
<212> TYPE: PRT
<213> ORGANISM: Artificial sequence
<220> FEATURE:
<223> OTHER INFORMATION: Synthetic Polypeptide

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asn Ile Asn Tyr Tyr Gly Lys Phe
    50                  55                  60

Lys Asp Lys Ala Thr Leu Thr Ala Asp Lys Ser Ala Asn Thr Ala Tyr
65                  70                  75                  80

Met Glu Leu Ser Ser Leu Arg Ser Glu Asp Thr Ala Val Tyr Phe Cys
                85                  90                  95

Ala Arg Ser Phe Leu Tyr Val Asp Phe Asp Tyr Trp Gly Gln Gly Thr
            100                 105                 110

Thr Leu Thr Val Ser
        115

<210> SEQ ID NO 57
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Glu Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Gly
                85                  90                  95
```

Thr His Val Pro Tyr Thr Phe Gly Gln Gly Thr Lys Leu Glu Ile Lys
            100                 105                 110
Arg

<210> SEQ ID NO 58
<211> LENGTH: 8
<212> TYPE: PRT
<213> ORGANISM: Artificial sequence
<220> FEATURE:
<223> OTHER INFORMATION: Synthetic Polypeptide

<400> SEQUENCE: 58

Gly Tyr Thr Phe Ser Asn Ser Trp
1               5

<210> SEQ ID NO 59
<211> LENGTH: 17
<212> TYPE: PRT
<213> ORGANISM: Artificial sequence
<220> FEATURE:
<223> OTHER INFORMATION: Synthetic Polypeptide

<400> SEQUENCE: 59

Leu Gln Trp Tyr Leu Gln Lys Pro Gly Glu Ser Pro Gln Leu Leu Ile
1               5                   10                  15
Tyr

<210> SEQ ID NO 60
<211> LENGTH: 12
<212> TYPE: PRT
<213> ORGANISM: Artificial sequence
<220> FEATURE:
<223> OTHER INFORMATION: Synthetic Polypeptide

<400> SEQUENCE: 60

Ser Phe Glu Asp Phe Trp Lys Gly Glu Asp Leu Ser
1               5                   10

<210> SEQ ID NO 61
<211> LENGTH: 15
<212> TYPE: PRT
<213> ORGANISM: Artificial sequence
<220> FEATURE:
<223> OTHER INFORMATION: Synthetic Polypeptide

<400> SEQUENCE: 61

Gly Gly Gly Gly Ser Gly Gly Gly Ser Gly Gly Gly Gly Ser
1               5                   10                  15

<210> SEQ ID NO 62
<211> LENGTH: 4
<212> TYPE: PRT
<213> ORGANISM: Artificial sequence
<220> FEATURE:
<223> OTHER INFORMATION: Synthetic Polypeptide

<400> SEQUENCE: 62

Cys Pro Pro Cys
1